US009451968B2

(12) United States Patent
Miller et al.

(10) Patent No.: US 9,451,968 B2
(45) Date of Patent: Sep. 27, 2016

(54) POWERED DRIVERS, INTRAOSSEOUS DEVICES AND METHODS TO ACCESS BONE MARROW

(75) Inventors: Larry J. Miller, Spring Branch, TX (US); David S. Bolleter, San Antonio, TX (US); Robert W. Titkemeyer, San Antonio, TX (US)

(73) Assignee: Vidacare LLC, Wayne, PA (US)

( * ) Notice: Subject to any disclaimer, the term of this patent is extended or adjusted under 35 U.S.C. 154(b) by 2345 days.

(21) Appl. No.: 12/061,944

(22) Filed: Apr. 3, 2008

(65) Prior Publication Data

US 2008/0215056 A1 Sep. 4, 2008

Related U.S. Application Data

(63) Continuation-in-part of application No. 11/253,959, filed on Oct. 19, 2005, now Pat. No. 8,506,568, which is a continuation-in-part of application No. 11/253,467, filed on Oct. 19, 2005, now Pat. No.
(Continued)

(51) Int. Cl.
*A61B 17/32* (2006.01)
*A61B 17/16* (2006.01)
(Continued)

(52) U.S. Cl.
CPC ......... *A61B 17/1628* (2013.01); *A61B 10/025* (2013.01); *A61B 17/1624* (2013.01); *A61B 17/32002* (2013.01); *A61B 17/3476* (2013.01); *A61B 17/1637* (2013.01); *A61B 17/32053* (2013.01); *A61B 17/3472* (2013.01); *A61B 90/11* (2016.02); *A61B 90/30* (2016.02);
(Continued)

(58) Field of Classification Search
CPC ................................. A61B 17/32002
USPC ........................... 606/79–81, 86 R
See application file for complete search history.

(56) References Cited

U.S. PATENT DOCUMENTS

| 1,539,637 A | 5/1925 | Bronner |
| 2,317,648 A | 4/1943 | Siqveland ............ 32/26 |

(Continued)

FOREIGN PATENT DOCUMENTS

| CA | 2138842 | 6/1996 | ............ A61M 19/00 |
| CA | 2 454 600 | 1/2004 | |

(Continued)

OTHER PUBLICATIONS

International PCT Search Report PCT/US03/17167, 8 pages, Mailed Sep. 16, 2003.
(Continued)

*Primary Examiner* — Christian Sevilla
(74) *Attorney, Agent, or Firm* — Baker & Hostetler LLP

(57) ABSTRACT

Apparatus and methods are provided to penetrate a bone and associated bone marrow using a powered driver. The powered driver may include a housing having a gear assembly, a motor and a power supply disposed therein. A penetrator assembly may be releasably engaged with one end of a drive shaft extending from the housing. The powered driver may include a light operable to illuminate an insertion site for the penetrator assembly. An indicator may be provided to show status of an associated power supply. An indicator may also be provided to show status of penetrating bone and/or associated bone marrow using a penetrator assembly. The apparatus may include an enable switch to prevent undesired operation of the powered driver.

20 Claims, 8 Drawing Sheets

Related U.S. Application Data 8,876,826, which is a continuation-in-part of application No. 10/449,476, filed on May 30, 2003, now Pat. No. 7,699,850.

(60) Provisional application No. 60/910,122, filed on Apr. 4, 2007, provisional application No. 60/384,756, filed on May 31, 2002.

(51) Int. Cl.
    *A61B 10/02*     (2006.01)
    *A61B 17/3205*     (2006.01)
    *A61B 17/34*     (2006.01)
    *A61B 17/00*     (2006.01)
    *A61M 5/158*     (2006.01)

(52) U.S. Cl.
CPC ..... *A61B2010/0258* (2013.01); *A61B 2017/0046* (2013.01); *A61B 2017/00398* (2013.01); *A61B 2017/00734* (2013.01); *A61M 5/158* (2013.01); *A61M 2005/1581* (2013.01); *A61M 2005/1585* (2013.01); *A61M 2210/02* (2013.01)

(56) References Cited

U.S. PATENT DOCUMENTS

| | | | | |
|---|---|---|---|---|
| 2,419,045 | A | 4/1947 | Whittaker | 128/305 |
| 2,773,501 | A | 12/1956 | Young | 128/221 |
| 3,022,596 | A | 2/1962 | Cannon et al. | |
| 3,104,448 | A | 9/1963 | Morrow et al. | |
| 3,120,845 | A | 2/1964 | Horner | 128/310 |
| 3,173,417 | A | 3/1965 | Horner | 128/305 |
| 3,175,554 | A | 3/1965 | Stewart | 128/2 |
| 3,507,276 | A | 4/1970 | Burgess et al. | 128/173 |
| 3,543,966 | A | 12/1970 | Ryan et al. | 222/94 |
| 3,734,207 | A | 5/1973 | Fishbein | |
| 3,815,605 | A | 6/1974 | Schmidt et al. | 128/305 |
| 3,835,860 | A | 9/1974 | Garretson et al. | 128/310 |
| 3,893,445 | A | 7/1975 | Hofsess | 128/2 B |
| 3,935,909 | A | 2/1976 | Mabuchi et al. | |
| 3,991,765 | A | 11/1976 | Cohen | 128/305 |
| 3,999,110 | A | 12/1976 | Ramstrom et al. | |
| 4,021,920 | A | 5/1977 | Kirschner et al. | 32/28 |
| 4,099,518 | A | 7/1978 | Baylis et al. | 600/567 |
| 4,124,026 | A | 11/1978 | Berner et al. | 606/104 |
| 4,142,517 | A | 3/1979 | Stavropoulos | 128/2 B |
| 4,170,993 | A | 10/1979 | Alvarez | 128/214 R |
| 4,185,619 | A | 1/1980 | Reiss | 128/1.1 |
| 4,194,505 | A | 3/1980 | Schmitz | 128/218 |
| 4,258,722 | A | 3/1981 | Sessions et al. | 128/753 |
| 4,262,676 | A | 4/1981 | Jamshidi | 128/753 |
| 4,306,570 | A | 12/1981 | Matthews | 128/754 |
| 4,333,459 | A | 6/1982 | Becker | 128/218 |
| 4,381,777 | A | 5/1983 | Garnier | 604/188 |
| 4,441,563 | A | 4/1984 | Walton, II | 173/163 |
| 4,469,109 | A | 9/1984 | Mehl | 128/753 |
| 4,484,577 | A | 11/1984 | Sackner et al. | 128/203.28 |
| 4,543,966 | A | 10/1985 | Islam et al. | 128/754 |
| 4,553,539 | A | 11/1985 | Morris | 128/132 D |
| 4,605,011 | A | 8/1986 | Naslund | 128/752 |
| 4,620,539 | A | 11/1986 | Andrews et al. | 128/303 |
| 4,646,731 | A | 3/1987 | Brower | 128/156 |
| 4,654,492 | A | 3/1987 | Koerner et al. | 200/153 P |
| 4,655,226 | A | 4/1987 | Lee | 128/754 |
| 4,659,329 | A | 4/1987 | Annis | 604/180 |
| 4,692,073 | A | 9/1987 | Martindell | |
| 4,711,636 | A | 12/1987 | Bierman | 604/180 |
| 4,713,061 | A | 12/1987 | Tarello et al. | 604/200 |
| 4,716,901 | A | 1/1988 | Jackson et al. | 128/343 |
| 4,723,945 | A | 2/1988 | Theiling | 604/232 |
| 4,758,225 | A | 7/1988 | Cox et al. | 604/126 |
| 4,762,118 | A | 8/1988 | Lia et al. | 128/4 |
| 4,772,261 | A | 9/1988 | Von Hoff et al. | 604/51 |
| 4,787,893 | A * | 11/1988 | Villette | A61C 19/08 433/118 |
| 4,793,363 | A | 12/1988 | Ausherman et al. | 128/754 |
| 4,867,158 | A | 9/1989 | Sugg | 128/305 |
| 4,919,146 | A | 4/1990 | Rhinehart et al. | 128/752 |
| 4,921,013 | A | 5/1990 | Spalink et al. | 137/614.05 |
| 4,935,010 | A | 6/1990 | Cox et al. | 604/122 |
| 4,940,459 | A | 7/1990 | Noce | 604/98 |
| 4,944,677 | A | 7/1990 | Alexandre | 433/165 |
| 4,969,870 | A | 11/1990 | Kramer et al. | 604/51 |
| 4,986,279 | A | 1/1991 | O'Neill | 128/754 |
| 5,002,546 | A | 3/1991 | Romano | 606/80 |
| 5,025,797 | A | 6/1991 | Baran | 128/754 |
| 5,036,860 | A | 8/1991 | Leigh et al. | 128/754 |
| 5,057,085 | A | 10/1991 | Kopans | 604/173 |
| 5,074,311 | A | 12/1991 | Hasson | 128/754 |
| 5,116,324 | A | 5/1992 | Brierley et al. | 604/180 |
| 5,120,312 | A | 6/1992 | Wigness et al. | 604/175 |
| 5,122,114 | A | 6/1992 | Miller et al. | 604/49 |
| 5,133,359 | A | 7/1992 | Kedem | 128/754 |
| 5,137,518 | A | 8/1992 | Mersch | 604/168 |
| 5,139,500 | A | 8/1992 | Schwartz | 606/96 |
| RE34,056 | E | 9/1992 | Lindgren et al. | 128/754 |
| 5,172,701 | A | 12/1992 | Leigh et al. | 128/753 |
| 5,172,702 | A | 12/1992 | Leigh et al. | 128/754 |
| 5,176,643 | A | 1/1993 | Kramer et al. | 604/135 |
| 5,195,985 | A | 3/1993 | Hall | 604/195 |
| 5,203,056 | A | 4/1993 | Funk et al. | 24/543 |
| 5,207,697 | A * | 5/1993 | Carusillo | A61B 17/1626 320/115 |
| 5,217,478 | A * | 6/1993 | Rexroth | 606/180 |
| 5,249,583 | A | 10/1993 | Mallaby | 128/754 |
| 5,257,632 | A | 11/1993 | Turkel et al. | 128/754 |
| 5,269,785 | A | 12/1993 | Bonutti | 606/80 |
| 5,279,306 | A | 1/1994 | Mehl | 128/753 |
| 5,312,364 | A | 5/1994 | Jacobs | 604/180 |
| 5,324,300 | A | 6/1994 | Elias et al. | 606/180 |
| 5,332,398 | A | 7/1994 | Miller et al. | 604/175 |
| 5,333,790 | A | 8/1994 | Christopher | 239/391 |
| 5,341,823 | A | 8/1994 | Manosalva et al. | 128/898 |
| 5,348,022 | A | 9/1994 | Leigh et al. | 128/753 |
| 5,357,974 | A | 10/1994 | Baldridge | 128/754 |
| 5,361,853 | A | 11/1994 | Takamura et al. | |
| 5,368,046 | A | 11/1994 | Scarfone et al. | 128/754 |
| 5,372,583 | A | 12/1994 | Roberts et al. | 604/51 |
| 5,383,859 | A | 1/1995 | Sewell, Jr. | 604/164 |
| 5,385,553 | A | 1/1995 | Hart et al. | 604/167 |
| 5,400,798 | A | 3/1995 | Baran | 128/754 |
| 5,405,348 | A | 4/1995 | Anspach et al. | 606/80 |
| 5,423,824 | A | 6/1995 | Akerfeldt et al. | 606/80 |
| 5,431,655 | A | 7/1995 | Melker et al. | 606/79 |
| 5,451,210 | A | 9/1995 | Kramer et al. | 604/137 |
| 5,484,442 | A | 1/1996 | Melker et al. | 606/79 |
| D369,858 | S | 5/1996 | Baker et al. | D24/112 |
| 5,526,821 | A | 6/1996 | Jamshidi | 128/753 |
| 5,529,580 | A | 6/1996 | Kusunoki et al. | 606/170 |
| 5,549,565 | A | 8/1996 | Ryan et al. | 604/167 |
| 5,554,154 | A | 9/1996 | Rosenberg | 606/80 |
| 5,556,399 | A | 9/1996 | Huebner et al. | 606/80 |
| 5,558,737 | A | 9/1996 | Brown et al. | 156/172 |
| 5,571,133 | A | 11/1996 | Yoon | 606/185 |
| 5,586,847 | A | 12/1996 | Mattern, Jr. et al. | 408/239 A |
| 5,591,188 | A | 1/1997 | Waisman | 606/182 |
| 5,595,186 | A | 1/1997 | Rubinstein et al. | 600/567 |
| 5,601,559 | A | 2/1997 | Melker et al. | 606/79 |
| 5,632,747 | A | 5/1997 | Scarborough et al. | 606/79 |
| 5,651,419 | A | 7/1997 | Holzer et al. | |
| 5,713,368 | A | 2/1998 | Leigh | 128/753 |
| 5,724,873 | A | 3/1998 | Hillinger | 81/451 |
| 5,733,262 | A | 3/1998 | Paul | 604/116 |
| 5,752,923 | A | 5/1998 | Terwilliger | 600/562 |
| 5,762,639 | A | 6/1998 | Gibbs | 604/272 |
| 5,766,221 | A | 6/1998 | Benderev et al. | 606/232 |
| 5,769,086 | A | 6/1998 | Ritchart et al. | 128/753 |
| 5,779,708 | A | 7/1998 | Wu | 606/80 |
| 5,800,389 | A | 9/1998 | Burney et al. | 604/93 |
| 5,801,454 | A * | 9/1998 | Leininger | 290/54 |
| 5,807,277 | A | 9/1998 | Swaim | 600/567 |

(56) References Cited

U.S. PATENT DOCUMENTS

| | | | | |
|---|---|---|---|---|
| 5,809,653 A * | 9/1998 | Everts | | A01D 34/90 15/328 |
| 5,810,826 A | 9/1998 | Akerfeldt et al. | | 606/80 |
| 5,817,052 A | 10/1998 | Johnson et al. | | 604/51 |
| 5,823,970 A | 10/1998 | Terwilliger | | 600/564 |
| D403,405 S | 12/1998 | Terwilliger | | D24/130 |
| 5,858,005 A | 1/1999 | Kriesel | | 604/180 |
| 5,868,711 A | 2/1999 | Kramer et al. | | 604/136 |
| 5,868,750 A | 2/1999 | Schultz | | 606/104 |
| 5,873,510 A | 2/1999 | Hirai et al. | | 227/130 |
| 5,885,226 A | 3/1999 | Rubinstein et al. | | 600/564 |
| 5,891,085 A | 4/1999 | Lilley et al. | | 604/68 |
| 5,911,701 A | 6/1999 | Miller et al. | | 604/22 |
| 5,911,708 A | 6/1999 | Teirstein | | 604/183 |
| 5,916,229 A | 6/1999 | Evans | | 606/171 |
| 5,919,172 A | 7/1999 | Golba, Jr. | | 604/272 |
| 5,924,864 A | 7/1999 | Loge et al. | | 433/118 |
| 5,927,976 A | 7/1999 | Wu | | 433/82 |
| 5,928,238 A | 7/1999 | Scarborough et al. | | 606/79 |
| 5,928,241 A * | 7/1999 | Menut | | A61B 17/162 279/143 |
| 5,941,706 A | 8/1999 | Ura | | 433/165 |
| 5,941,851 A | 8/1999 | Coffey et al. | | 604/131 |
| 5,960,797 A | 10/1999 | Kramer et al. | | 128/899 |
| 5,980,545 A | 11/1999 | Pacala et al. | | 606/170 |
| 5,984,020 A | 11/1999 | Meyer et al. | | |
| 5,993,417 A | 11/1999 | Yerfino et al. | | 604/110 |
| 5,993,454 A | 11/1999 | Longo | | 606/80 |
| 6,007,496 A | 12/1999 | Brannon | | 600/565 |
| 6,017,348 A | 1/2000 | Hart et al. | | 606/79 |
| 6,018,094 A | 1/2000 | Fox | | 623/11 |
| 6,022,324 A | 2/2000 | Skinner | | 600/566 |
| 6,027,458 A | 2/2000 | Janssens | | 600/567 |
| 6,033,369 A | 3/2000 | Goldenberg | | 600/567 |
| 6,033,411 A | 3/2000 | Preissman | | 606/99 |
| 6,059,806 A * | 5/2000 | Hoegerle | | A61B 17/1628 606/180 |
| 6,063,037 A | 5/2000 | Mittermeier et al. | | 600/567 |
| 6,071,284 A | 6/2000 | Fox | | 606/80 |
| 6,080,115 A | 6/2000 | Rubinstein | | 600/567 |
| 6,083,176 A | 7/2000 | Terwilliger | | 600/562 |
| 6,086,543 A | 7/2000 | Anderson et al. | | 600/567 |
| 6,086,544 A | 7/2000 | Hibner et al. | | 600/568 |
| 6,092,355 A * | 7/2000 | Ishmael | | 56/11.9 |
| 6,096,042 A | 8/2000 | Herbert | | 606/80 |
| 6,102,915 A | 8/2000 | Bresler et al. | | 606/80 |
| 6,106,484 A | 8/2000 | Terwilliger | | 600/568 |
| 6,110,128 A | 8/2000 | Andelin et al. | | 600/566 |
| 6,110,129 A | 8/2000 | Terwilliger | | 600/567 |
| 6,110,174 A | 8/2000 | Nichter | | 606/72 |
| 6,120,462 A | 9/2000 | Hibner et al. | | 600/566 |
| 6,126,670 A | 10/2000 | Walker et al. | | |
| 6,135,769 A | 10/2000 | Kwan | | 433/80 |
| 6,159,163 A | 12/2000 | Strauss et al. | | 600/566 |
| 6,162,203 A | 12/2000 | Haaga | | 604/272 |
| 6,183,442 B1 | 2/2001 | Athanasiou et al. | | 604/154 |
| 6,210,376 B1 | 4/2001 | Grayson | | 604/264 |
| 6,217,561 B1 | 4/2001 | Gibbs | | 604/264 |
| 6,221,029 B1 | 4/2001 | Mathis et al. | | 600/564 |
| 6,228,049 B1 | 5/2001 | Schroeder et al. | | 604/93.01 |
| 6,228,088 B1 | 5/2001 | Miller et al. | | 606/80 |
| 6,238,355 B1 | 5/2001 | Daum | | 600/567 |
| 6,247,928 B1 | 6/2001 | Meller et al. | | 433/80 |
| 6,248,110 B1 | 6/2001 | Reiley et al. | | 606/93 |
| 6,257,351 B1 | 7/2001 | Ark et al. | | 173/178 |
| 6,273,715 B1 | 8/2001 | Meller et al. | | 433/80 |
| 6,273,862 B1 | 8/2001 | Privitera et al. | | 600/568 |
| 6,283,925 B1 | 9/2001 | Terwilliger | | 600/568 |
| 6,283,970 B1 | 9/2001 | Lubinus | | 606/80 |
| 6,287,114 B1 | 9/2001 | Meller et al. | | 433/80 |
| 6,302,852 B1 | 10/2001 | Fleming, III et al. | | 600/567 |
| 6,309,358 B1 | 10/2001 | Okubo | | 600/466 |
| 6,312,394 B1 | 11/2001 | Fleming, III | | 600/567 |
| 6,315,737 B1 | 11/2001 | Skinner | | 600/566 |
| 6,325,806 B1 | 12/2001 | Fox | | 606/80 |
| 6,328,701 B1 | 12/2001 | Terwilliger | | 600/567 |
| 6,328,744 B1 | 12/2001 | Harari et al. | | 606/80 |
| 6,358,252 B1 | 3/2002 | Shapira | | 606/80 |
| 6,402,701 B1 | 6/2002 | Kaplan et al. | | 600/567 |
| 6,419,490 B1 | 7/2002 | Kitchings Weathers, Jr. | | 433/165 |
| 6,425,888 B1 | 7/2002 | Embleton et al. | | 604/290 |
| 6,428,487 B1 | 8/2002 | Burdorff et al. | | 600/568 |
| 6,443,910 B1 | 9/2002 | Krueger et al. | | 600/567 |
| 6,468,248 B1 | 10/2002 | Gibbs | | 604/164.01 |
| 6,478,751 B1 | 11/2002 | Krueger et al. | | 600/566 |
| 6,488,636 B2 | 12/2002 | Bryan et al. | | 600/565 |
| 6,523,698 B1 | 2/2003 | Dennehey et al. | | 210/435 |
| 6,527,736 B1 | 3/2003 | Attinger et al. | | 604/43 |
| 6,527,778 B2 | 3/2003 | Athanasiou et al. | | 606/80 |
| 6,540,694 B1 | 4/2003 | Van Bladel et al. | | 600/564 |
| 6,547,511 B1 | 4/2003 | Adams | | 414/46.4 |
| 6,547,561 B2 | 4/2003 | Meller et al. | | 433/80 |
| 6,554,779 B2 | 4/2003 | Viola et al. | | 600/568 |
| 6,555,212 B2 | 4/2003 | Boiocchi et al. | | 428/295.4 |
| 6,582,399 B1 | 6/2003 | Smith et al. | | 604/152 |
| 6,585,622 B1 | 7/2003 | Shum et al. | | 482/8 |
| 6,595,911 B2 | 7/2003 | LoVuolo | | 600/30 |
| 6,595,979 B1 | 7/2003 | Epstein et al. | | 604/506 |
| 6,613,054 B2 | 9/2003 | Scribner et al. | | 606/93 |
| 6,616,632 B2 | 9/2003 | Sharp et al. | | 604/117 |
| 6,620,111 B2 | 9/2003 | Stehens et al. | | 600/567 |
| 6,626,848 B2 | 9/2003 | Neuenfeldt | | 600/564 |
| 6,626,887 B1 | 9/2003 | Wu | | 604/512 |
| 6,638,235 B2 | 10/2003 | Miller et al. | | 600/566 |
| 6,656,133 B2 | 12/2003 | Voegele et al. | | 600/568 |
| 6,689,072 B2 | 2/2004 | Kaplan et al. | | 600/567 |
| 6,702,760 B2 | 3/2004 | Krause et al. | | 600/564 |
| 6,702,761 B1 | 3/2004 | Damadian et al. | | 600/576 |
| 6,706,016 B2 | 3/2004 | Cory et al. | | 604/117 |
| 6,716,192 B1 | 4/2004 | Orosz, Jr. | | 604/117 |
| 6,716,215 B1 | 4/2004 | David et al. | | 606/80 |
| 6,716,216 B1 | 4/2004 | Boucher et al. | | 606/86 |
| 6,730,043 B2 | 5/2004 | Krueger et al. | | 606/567 |
| 6,730,044 B2 | 5/2004 | Stephens et al. | | 600/568 |
| 6,749,576 B2 | 6/2004 | Bauer | | 600/567 |
| 6,752,768 B2 | 6/2004 | Burdorff et al. | | 600/568 |
| 6,752,816 B2 | 6/2004 | Culp et al. | | 606/170 |
| 6,758,824 B1 | 7/2004 | Miller et al. | | 600/568 |
| 6,761,726 B1 | 7/2004 | Findlay et al. | | 606/182 |
| 6,796,957 B2 | 9/2004 | Carpenter et al. | | 604/93.01 |
| 6,846,314 B2 | 1/2005 | Shapira | | 606/80 |
| 6,849,051 B2 | 2/2005 | Sramek et al. | | 600/565 |
| 6,855,148 B2 | 2/2005 | Foley et al. | | 606/86 |
| 6,860,860 B2 | 3/2005 | Viola | | 600/564 |
| 6,875,183 B2 | 4/2005 | Cervi | | 600/567 |
| 6,875,219 B2 | 4/2005 | Arramon et al. | | 606/92 |
| 6,884,245 B2 | 4/2005 | Spranza | | 606/79 |
| 6,887,209 B2 | 5/2005 | Kadziauskas et al. | | 600/565 |
| 6,890,308 B2 | 5/2005 | Islam | | 600/564 |
| 6,905,486 B2 | 6/2005 | Gibbs | | 604/264 |
| 6,930,461 B2 | 8/2005 | Rutkowski | | 318/567 |
| 6,942,669 B2 | 9/2005 | Kurc | | 606/80 |
| 6,969,373 B2 | 11/2005 | Schwartz et al. | | 604/170.03 |
| 7,008,381 B2 | 3/2006 | Janssens | | 600/564 |
| 7,008,383 B1 | 3/2006 | Damadian et al. | | 600/567 |
| 7,008,394 B2 | 3/2006 | Geise et al. | | 615/6.15 |
| 7,025,732 B2 | 4/2006 | Thompson et al. | | 600/654 |
| 7,063,672 B2 | 6/2006 | Schramm | | 600/564 |
| 7,137,985 B2 | 11/2006 | Jahng | | 606/61 |
| 7,207,949 B2 | 4/2007 | Miles et al. | | 600/554 |
| 7,226,450 B2 | 6/2007 | Athanasiou et al. | | 606/80 |
| 7,229,401 B2 | 6/2007 | Kindlein | | 600/7 |
| 7,565,935 B1 | 7/2009 | Phillips | | |
| 2001/0005778 A1 | 6/2001 | Ouchi | | 600/564 |
| 2001/0014439 A1 | 8/2001 | Meller et al. | | 433/50 |
| 2001/0047183 A1 | 11/2001 | Privitera et al. | | 606/170 |
| 2001/0053888 A1 | 12/2001 | Athanasiou et al. | | 604/154 |
| 2002/0042581 A1 | 4/2002 | Cervi | | 600/567 |
| 2002/0050364 A1 | 5/2002 | Suzuki et al. | | |
| 2002/0055713 A1 | 5/2002 | Gibbs | | 604/164.01 |
| 2002/0120212 A1 | 8/2002 | Ritchart et al. | | 600/567 |
| 2002/0138021 A1 | 9/2002 | Pflueger | | 600/565 |
| 2002/0158102 A1 | 10/2002 | Patton et al. | | |

(56) References Cited

U.S. PATENT DOCUMENTS

| | | | | |
|---|---|---|---|---|
| 2003/0028146 A1 | 2/2003 | Aves | | 604/164.06 |
| 2003/0032939 A1 | 2/2003 | Gibbs | | 604/510 |
| 2003/0036747 A1 | 2/2003 | Ie et al. | | 606/1 |
| 2003/0050574 A1 | 3/2003 | Krueger | | 600/567 |
| 2003/0114858 A1 | 6/2003 | Athanasiou et al. | | 606/80 |
| 2003/0125639 A1 | 7/2003 | Fisher et al. | | 600/564 |
| 2003/0153842 A1 | 8/2003 | Lamoureux et al. | | 600/564 |
| 2003/0191414 A1 | 10/2003 | Reiley et al. | | 600/567 |
| 2003/0195436 A1 | 10/2003 | Van Bladel et al. | | 600/584 |
| 2003/0195524 A1 | 10/2003 | Barner | | 606/119 |
| 2003/0199787 A1 | 10/2003 | Schwindt | | 600/568 |
| 2003/0216667 A1 | 11/2003 | Viola | | 600/564 |
| 2003/0225344 A1 | 12/2003 | Miller | | 600/568 |
| 2003/0225364 A1 | 12/2003 | Kraft et al. | | 604/35 |
| 2003/0225411 A1 | 12/2003 | Miller | | 606/80 |
| 2004/0019297 A1 | 1/2004 | Angel | | 600/564 |
| 2004/0019299 A1 | 1/2004 | Ritchart et al. | | 600/567 |
| 2004/0034280 A1 | 2/2004 | Privitera et al. | | 600/170 |
| 2004/0049128 A1 | 3/2004 | Miller et al. | | 600/566 |
| 2004/0064136 A1 | 4/2004 | Papineau et al. | | 606/41 |
| 2004/0073139 A1 | 4/2004 | Hirsch et al. | | 600/564 |
| 2004/0092946 A1 | 5/2004 | Bagga et al. | | 606/93 |
| 2004/0153003 A1 | 8/2004 | Cicenas et al. | | 600/564 |
| 2004/0158172 A1 | 8/2004 | Hancock | | 600/564 |
| 2004/0158173 A1 | 8/2004 | Voegele et al. | | 600/568 |
| 2004/0162505 A1 | 8/2004 | Kaplan et al. | | 600/567 |
| 2004/0191897 A1 | 9/2004 | Muschler | | 435/325 |
| 2004/0210161 A1 | 10/2004 | Burdorff et al. | | 600/566 |
| 2004/0215102 A1 | 10/2004 | Ikehara et al. | | 600/562 |
| 2004/0220497 A1 | 11/2004 | Findlay et al. | | 600/562 |
| 2005/0027210 A1 | 2/2005 | Miller | | 600/567 |
| 2005/0040060 A1 | 2/2005 | Andersen et al. | | 206/363 |
| 2005/0075581 A1 | 4/2005 | Schwindt | | 600/568 |
| 2005/0085838 A1 | 4/2005 | Thompson et al. | | 606/170 |
| 2005/0101880 A1 | 5/2005 | Cicenas et al. | | 600/567 |
| 2005/0113716 A1 | 5/2005 | Mueller, Jr. et al. | | 600/568 |
| 2005/0116673 A1* | 6/2005 | Carl | | A61B 17/14 318/432 |
| 2005/0124915 A1 | 6/2005 | Eggers et al. | | 600/568 |
| 2005/0131345 A1 | 6/2005 | Miller | | 604/117 |
| 2005/0148940 A1 | 7/2005 | Miller | | 604/187 |
| 2005/0165328 A1 | 7/2005 | Heske et al. | | 600/566 |
| 2005/0165403 A1 | 7/2005 | Miller | | 606/79 |
| 2005/0165404 A1 | 7/2005 | Miller | | 606/80 |
| 2005/0171504 A1 | 8/2005 | Miller | | 604/506 |
| 2005/0182394 A1 | 8/2005 | Spero et al. | | 606/21 |
| 2005/0200087 A1 | 9/2005 | Vasudeva et al. | | 279/143 |
| 2005/0203439 A1 | 9/2005 | Heske et al. | | 600/566 |
| 2005/0209530 A1 | 9/2005 | Pflueger | | 600/567 |
| 2005/0215921 A1 | 9/2005 | Hibner et al. | | 600/566 |
| 2005/0228309 A1 | 10/2005 | Fisher et al. | | 600/562 |
| 2005/0261693 A1 | 11/2005 | Miller et al. | | 606/80 |
| 2006/0011506 A1 | 1/2006 | Riley | | 206/570 |
| 2006/0015066 A1 | 1/2006 | Turieo et al. | | 604/136 |
| 2006/0036212 A1 | 2/2006 | Miller | | 604/48 |
| 2006/0052790 A1 | 3/2006 | Miller | | 606/80 |
| 2006/0074345 A1 | 4/2006 | Hibner | | 600/566 |
| 2006/0079774 A1 | 4/2006 | Anderson | | 600/442 |
| 2006/0089565 A1 | 4/2006 | Schramm | | 600/566 |
| 2006/0122535 A1 | 6/2006 | Daum | | 600/565 |
| 2006/0129082 A1 | 6/2006 | Rozga | | 604/6.04 |
| 2006/0144548 A1 | 7/2006 | Beckman et al. | | 163/1 |
| 2006/0149163 A1 | 7/2006 | Hibner et al. | | 600/566 |
| 2006/0151188 A1 | 7/2006 | Bodine et al. | | |
| 2006/0167377 A1 | 7/2006 | Ritchart et al. | | 600/566 |
| 2006/0167378 A1 | 7/2006 | Miller | | 600/566 |
| 2006/0167379 A1 | 7/2006 | Miller | | 600/566 |
| 2006/0184063 A1 | 8/2006 | Miller | | 600/566 |
| 2006/0189940 A1 | 8/2006 | Kirsch | | 604/164.1 |
| 2007/0016100 A1 | 1/2007 | Miller | | 600/567 |
| 2007/0049945 A1 | 3/2007 | Miller | | 606/86 |
| 2007/0149920 A1 | 6/2007 | Michels et al. | | 604/93.01 |
| 2007/0213735 A1 | 9/2007 | Sandat et al. | | 606/79 |
| 2007/0270775 A1 | 11/2007 | Miller et al. | | 604/506 |
| 2008/0015467 A1 | 1/2008 | Miller | | 600/568 |
| 2008/0015468 A1 | 1/2008 | Miller | | 600/568 |
| 2008/0045857 A1 | 2/2008 | Miller | | 600/566 |
| 2008/0045860 A1 | 2/2008 | Miller et al. | | 600/567 |
| 2008/0045861 A1 | 2/2008 | Miller et al. | | 600/567 |
| 2008/0045965 A1 | 2/2008 | Miller et al. | | 606/80 |
| 2008/0087448 A1 | 4/2008 | Happ | | |
| 2008/0140014 A1 | 6/2008 | Miller et al. | | 604/180 |
| 2008/0215056 A1 | 9/2008 | Miller et al. | | 606/80 |
| 2008/0221580 A1 | 9/2008 | Miller et al. | | 606/80 |

FOREIGN PATENT DOCUMENTS

| | | | | |
|---|---|---|---|---|
| DE | 10057931 A1 | 11/2000 | | A61B 17/32 |
| EP | 517000 | 12/1992 | | A61M 5/168 |
| EP | 0807412 A1 | 11/1997 | | A61B 17/32 |
| EP | 1099450 | 5/2001 | | A61M 5/32 |
| EP | 1314452 | 5/2003 | | |
| FR | 853349 | 3/1940 | | |
| FR | 2457105 | 5/1979 | | |
| FR | 2516386 | 11/1981 | | |
| GB | 2130890 A | 6/1984 | | |
| JP | 1052433 | 2/1989 | | A61B 1/00 |
| WO | 93/07819 | 4/1993 | | A61B 17/32 |
| WO | 96/31164 | 10/1996 | | A61B 17/34 |
| WO | 98/06337 | 2/1998 | | A61B 17/16 |
| WO | 99/18866 | 4/1999 | | A61B 17/34 |
| WO | 99/52444 | 10/1999 | | A61B 17/00 |
| WO | 00/56220 | 9/2000 | | A61B 10/00 |
| WO | 01/78590 | 10/2001 | | A61B 5/00 |
| WO | 02/41792 A1 | 5/2002 | | A61B 17/16 |
| WO | 0241792 | 5/2002 | | A61B 17/16 |
| WO | 02096497 | 12/2002 | | A61M 31/00 |
| WO | 2005110259 | 11/2005 | | A61B 17/88 |
| WO | 2005112800 | 12/2005 | | A61B 17/34 |
| WO | 2008081438 | 7/2008 | | |

OTHER PUBLICATIONS

International PCT Search Report PCT/US03/17203, 8 pages, Mailed Sep. 16, 2003.

International PCT Search Report PCT/US2004/037753, 6 pages, Mailed Apr. 19, 2005.

Communication relating to the results of the partial International Search Report for PCT/US2005/002484, 6 pages, Mailed May 19, 2005.

International PCT Search Report and Written Opinion PCT/US2004/037753, 16 pages, Mailed Jul. 8, 2005.

International PCT Search Report and Written Opinion PCT/US2005/002484, 15 pages, Mailed Jul. 22, 2005.

Cummins, Richard O., et al, "ACLS-Principles and Practice", ACLS—The Reference Textbook, American Heart Association, pp. 214-218, 2003.

Riley et al., "A Pathologist's Perspective on Bone Marrow Aspiration Biopsy: I. Performing a Bone Marrow Examination," Journal of Clinical Laboratory Analysis 18, pp. 70-90, 2004.

International Preliminary Report on Patentability PCT/US2005/002484, 9 pages, Mailed Aug. 3, 2006.

Official Action for European Application No. 03756317.8 (4 pages), Dec. 28, 2006.

International Search Report and Written Opinion for International Application No. PCT/US2006/025201 (18 pages), Jan. 29, 2007.

Pediatrics, Official Journal of the American Academy of Pediatrics, Pediatrics, 2005 American Heart Association Guidelines for Cardiopulmonary Resuscitation and Emergency Cardiovascular Care of Pediatric and Neonatal Patients:Pediatric Advanced Life Support, Downloaded from www.pediatrics.org, Feb. 21, 2007.

Liakat A. Parapia, Trepanning or trephines: a history of bone marrow biopsy, British Journal of Haematology, pp. 14-19 2007, Date 2007.

Australian Exam Report on Patent Application No. 2003240970, 2 pages, Oct. 15, 2007.

Pediatric Emergency, Intraosseous Infusion for Administration of Fluids and Drugs, www.cookgroup.com, 1 pg, 2000.

Michael Trotty, "Technology (A Special Report)—The Wall Street Journal 2008 Technology Innovation Awards—This years winners

(56) References Cited

OTHER PUBLICATIONS include: an IV alternative, a better way to make solar panels, a cheap, fuel efficient car and a better way to see in the dark", The Wall Street Journal, Factiva, 5 pages, 2008.
Buckley et al., CT-guided bone biopsy: Initial experience with commercially available hand held Black and Decker drill, European Journal of Radiology 61, pp. 176-180, 2007.
Hakan et al., CT-guided Bone BiopsyPerformed by Means of Coaxial Bopsy System with an Eccentric Drill, Radiology, pp. 549-552, Aug. 1993.
European Search Report 08158699.2-1265, 4 pages, Aug. 2008.
International Search Report and Written Opinion, PCT/US2007/078204, 14 pages, Mailing Date May 15, 2008.
International Search Report and Written Opinion, PCT/US08/52943, 8 pages, Mailing Date Sep. 26, 2008.
European Office Action Communication, Application No. 08158699.2-1265/1967142, 10 pages, Nov. 4, 2008.
Gunal et al., Compartment Syndrome After Intraosseous Infusion: An Expiremental Study in Dogs, Journal of Pediatric Surgery, vol. 31, No. 11, pp. 1491-1493, Nov. 1996.
International Search Report, PCT/US2007/072217, 20 pages, Mailing Date Mar. 31, 2008.
International Search Report, PCT/US2007/072209, 18 pages, Mailing Date Apr. 25, 2008.
International Search Report, PCT/US2006/025201, 12 pages, Mailing Date Feb. 7, 2008.
Communication Pursuant to Article 94(3) EPC, Application No. 05 712 091.7-1265, 4 pages, Apr. 8, 2008.
Notification of the First Chinese Office Action, Application No. 200580003261.8, 3 pages, Mar. 21, 2008.
International Search Report and Written Opinion, PCT/US08/500346, 12 pages, Mailing Date May 22, 2008.
PCT Invitation to Pay Additional Fees, PCT/US2007/072209, 9 pages, Mailing Dec. 3, 2007.
"Proven reliability for quality bone marrow samples", Special Procedures, Cardinal Health, 6 pages, 2003.
F.A.S.T. 1 Intraosseous Infusion System with Depth-Control Mechanism Brochure, 6 pages, 2000.
BioAccess.com, Single Use Small Bone Power Tool—How It Works, 1 pg, Printed Jun. 9, 2008.
International Search Report and Written Opinion, PCT/US2007/078203, 15 pages, Mailing Date May 13, 2008.
International Search Report and Written Opinion, PCT/US2007/072202, 17 pages, Mailing Date Mar. 25, 2008.
International Search Report and Written Opinion, PCT/US2007/078207, 13 pages, Mailing Date Apr. 7, 2008.
International Search Report and Written Opinion, PCT/US2007/078205, 13 pages, Mailing date Sep. 11, 2007.
European Office Action EP03731475.4, 4 pages, Oct. 11, 2007.
U.S. Appl. No. 11/427,501 Non Final Office Action, 14 pages, Mailed Aug. 7, 2008.
Chinese Office Action, Application No. 2005800003261, (with English translation), (9 pgs), Jan. 16, 2009.
International Preliminary Report on Patentability, PCT/US/2007/078203, 13 pages, Mar. 26, 2009.
International Preliminary Report on Patentability, PCT/US/2007/078207, 10 pages, Mar. 26, 2009.
International Preliminary Report on Patentability, PCT/US/2007/078205, 10 pages, Mar. 26, 2009.
International Preliminary Report on Patentability, PCT/US/2007/078204, 11 pages, Apr. 2, 2009.
Vidacare Corporation Comments to Intraosseous Vascular Access Position Paper, Infusion Nurses Society, 6 pages, May 4, 2009.
International Preliminary Report on Patentability, PCT/US/2007/072209, 10 pages, May 14, 2009.
Japanese Office Action, Application No. 2004-508,670, (with English summary), (13 pgs), Apr. 21, 2009.
PCT Preliminary Report on Patentability, PCT/US/2008/050346, (8 pgs), Jul. 23, 2009.
Japanese Office Action, Application No. 2004-508,669, (with English summary), (9 pgs), Aug. 3, 2009.
Chinese Office Action, Application No. 200780000590.6, (with English translation), (13 pgs), Aug. 21, 2009.
European Office Action and Search Report, Application No. 09150973.7, (8 pgs), Oct. 23, 2009.
Chinese Office Action with English translation; Application No. 200910006631.3; pp. 12, Mar. 11, 2010.
European Extended Search Report, Application No. EP10153350.3, 5 pages, Mar. 11, 2010.
European Extended Search Report, Application No. EP08021732.6, 7 pages, Nov. 13, 2009.
European Office Action; Application No. 09 155 111.9-2310; pp. 3, Nov. 25, 2009.
Chinese Office Action with English translation; Application No. 200910006631.3; pp. 13, Mar. 11, 2010.
Taiwan Office Action , Application No. 94102179 (with English translation); 12 pages, May 13, 2010.
Chinese Office Action with English translation; Application No. 200780001198.3; pp. 13, Apr. 27, 2010.
Office Action issued in Chinese Application No. 200910006631.3, dated Mar. 22, 2011.
Non-Final Office Action, U.S. Appl. No. 10/449,476, 8 pages, Oct. 29, 2008.
Åström, K.G., "Automatic Biopsy Instruments Used Through a Coaxial Bone Biopsy System with an Eccentric Drill Tip," Acta Radiologica, 1995; 36:237-242, May 1995.
Åström, K. Gunnar O., "CT-guided Transsternal Core Biopsy of Anterior Mediastinal Masses," Radiology 1996; 199:564-567, May 1996.
International Preliminary Report on Patentability, PCT/US2007/072202, 10 pages, Mailed Jan. 15, 2009.
International Preliminary Report on Patentability, PCT/US2007/072217, 11 pages, Mailed Feb. 12, 2009.
State Intellectual Property Office of the People's Republic of China, First Office Action issued for Chinese Patent Application No. 200880000182.5, dated Sep. 10, 2010.
State Intellectual Property Office of the People's Republic of China, Second Office Action issued for Chinese Patent Application No. 200880000182.5, dated Mar. 12, 2012.
State Intellectual Property Office of the People'S Republic of China, Third Office Action issued for Chinese Patent Application No. 200880000182.5, dated Mar. Dec. 13, 2012.
State Intellectual Property Office of the People'S Republic of China, Rejection Decision issued for Chinese Patent Application No. 200880000182.5, dated Jun. 27, 2013.
State Intellectual Property Office of the People'S Republic of China, Reexamination Decision Issued for Chinese Patent Application No. 200880000182.5, dated Nov. 20, 2013.
European Patent Office, Communication from Examining Division for European Patent Application No. 08799753.2, dated May 18, 2015.
European Patent Office, Communication from Examining Division for European Patent Application No. 08799753.2, dated Sep. 29, 2014.
European Patent Office, Communication from Examining Division for European Patent Application No. 08799753.2, dated Apr. 10, 2014.
European Patent Office, European Search Report for European Patent Application No. 08799753.2, dated May 23, 2013.

\* cited by examiner

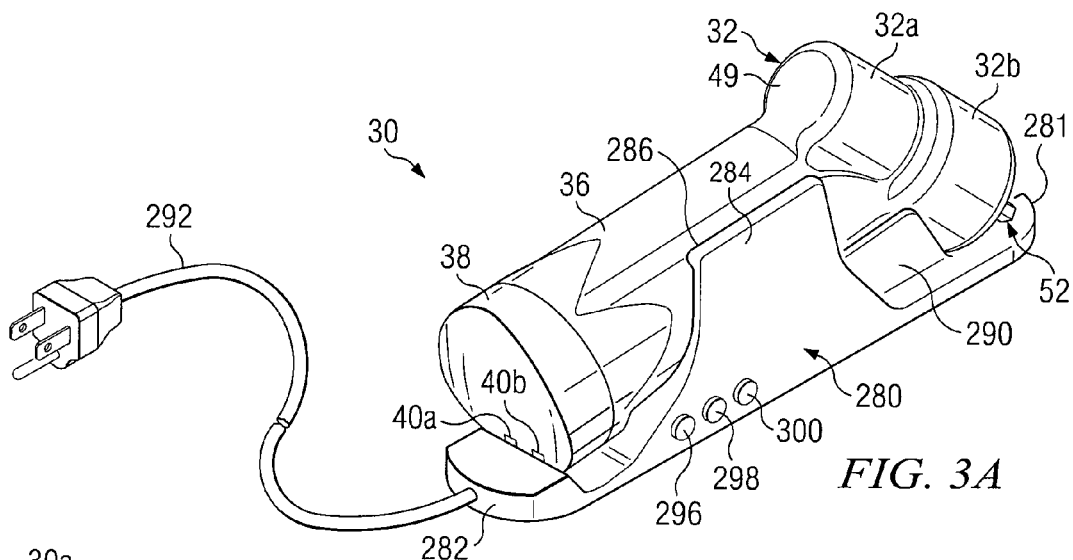
*FIG. 3A*
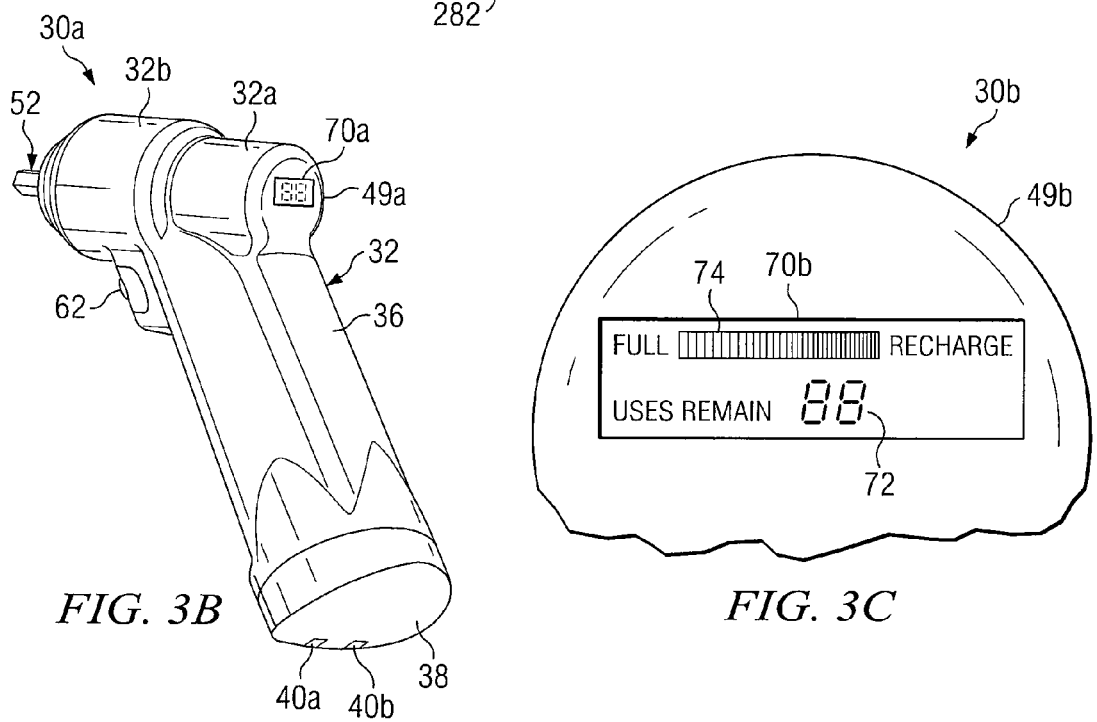
*FIG. 3B*
*FIG. 3C*
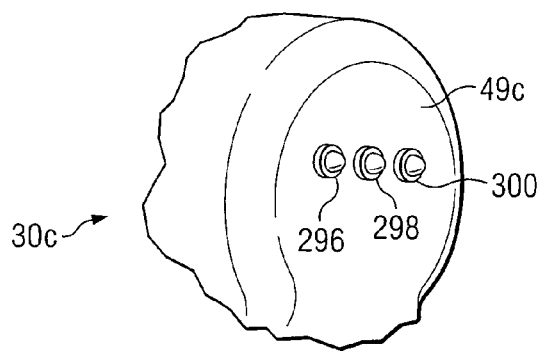
*FIG. 3D*

POWERED DRIVERS, INTRAOSSEOUS DEVICES AND METHODS TO ACCESS BONE MARROW

RELATED APPLICATIONS

This Application claims the benefit of U.S. Provisional Patent Application Ser. No. 60/910,122 entitled "Powered Drivers, Intraosseous Device and Methods to Access Bone Marrow" filed Apr. 4, 2007.

This application is a continuation-in-part of U.S. patent application Ser. No. 10/449,476 entitled "Apparatus and Method to Access to Bone Marrow" filed May 30, 2003.

This application is a continuation-in-part of U.S. patent application Ser. No. 11/253,467 entitled "Apparatus and Method to Access Bone Marrow" filed Oct. 19, 2005.

This application is a continuation-in-part of U.S. patent application Ser. No. 11/253,959 entitled "Method and Apparatus to Access Bone Marrow" filed Oct. 19, 2005.

TECHNICAL FIELD

The present disclosure is related in general to medical devices operable to access bone marrow and specifically to apparatus and methods for penetrating a bone and associated bone marrow with a powered driver and inserting an intraosseous device into the bone marrow.

BACKGROUND OF THE DISCLOSURE

Every year, millions of patients are treated for life-threatening emergencies in the United States. Such emergencies include shock, trauma, cardiac arrest, drug overdoses, diabetic ketoacidosis, arrhythmias, burns, and status epilepticus just to name a few. For example, according to the American Heart Association, more than 1,500,000 patients suffer from heart attacks (myocardial infarctions) every year, with over 500,000 of them dying from its devastating complications.

Obtaining satisfactorily vascular access may be a critical problem in approximately five (5%) percent to ten (10%) percent of patients treated in either prehospital or hospital settings. In the U.S. approximately six million patients annually may experience problems with traditional intravenous access. An essential element for treating medical emergencies is rapid establishment of vascular access to administer drugs and fluids directly into the circulatory system. Whether in an ambulance by paramedics, or in an emergency room by emergency specialists, the goal is the same—administer life-saving drugs and fluids. To a large degree, the ability to successfully treat such critical emergencies is dependent on skill and luck of an operator in accomplishing vascular access.

While it is relatively easy to start an IV on many patients, doctors, nurses and paramedics often experience great difficulty establishing IV access in some patients. These patients are probed repeatedly with sharp needles in an attempt to solve this problem and may require an invasive procedure to finally establish an intravenous route. A further complicating factor in achieving IV access occurs "in the field" (e.g., at the scene of an accident or during ambulance transport) where it is difficult to see the target and/or excessive motion makes accessing the venous system very difficult.

In the case of some patients (e.g., those with chronic disease or the elderly), the availability of easily-accessible veins may be depleted. Other patients may have no available IV sites due to anatomical scarcity of peripheral veins, obesity, extreme dehydration, and/or previous IV drug use. For these patients, finding a suitable site for administering lifesaving drugs becomes a monumental and frustrating task. While morbidity and mortality statistics are not generally available, it is known that many patients with life-threatening emergencies have died of ensuing complications because access to the vascular system with life-saving IV therapy was delayed or simply not possible. For such patients, an alternative approach is required.

Powered drivers associated with intraosseous (IO) devices typically include a housing with various types of motors and/or gear assemblies disposed therein. A rotatable shaft may be disposed within the housing and connected with a gear assembly. Various types of fittings, connections, connectors and/or connector receptacles may be provided at one end of the rotatable shaft extending from the housing to releasably engage an IO device with the powered driver.

Examples of powered drivers are shown in pending patent application Ser. No. 10/449,503 filed May 30, 2003 entitled "Apparatus and Method to Provide Emergency Access To Bone Marrow," Ser. No. 10/449,476 filed May 30, 2003 entitled "Apparatus and Method to Access Bone Marrow," and Ser. No. 11/042,912 filed Jan. 25, 2005 entitled "Manual Intraosseous Device."

Vascular system access may be essential for treatment of many serious diseases, chronic conditions and acute emergency situations. Yet, many patients experience extreme difficulty obtaining effective treatment because of inability to obtain or maintain intravenous (IV) access. An intraosseous (IO) space provides a direct conduit to a patent's vascular system and systemic circulation. Therefore, IO access is generally an effective route to administer a wide variety of drugs, other medications and fluids equivalent to IV access. Rapid IO access offers great promise for almost any serious emergency that requires vascular access to administer life saving drugs, other medications and/or fluids when traditional IV access is difficult or impossible.

Bone marrow typically includes blood, blood forming cells, and connective tissue disposed in an intraosseous space or cavity surrounded by compact bone. Long bones such as the tibia typically have an elongated central cavity filled with yellow bone marrow and adipose or connective tissue. Such cavities may also be referred to as a "medullary cavity", "bone marrow cavity" and/or "intraosseous space."

Compact bone disposed nearer the anterior or dorsal surface shall be referred to as "anterior compact bone" or "anterior bone cortex." Compact bone disposed farther from the dorsal or anterior surface may be referred to as "posterior compact bone" or "posterior bone cortex."

The upper tibia proximate a patient's knee or the humeral head proximate a patient's shoulder may be used as insertion sites for an IO device to establish access with the patient's vascular system. Sternal access may also be used as an insertion site. Availability of multiple intraosseous insertion sites and associated target areas in adjacent bone marrow have proven to be especially important in applications such as emergency treatment of battlefield casualties or other mass casualty situations. Teachings of the present disclosure may be used at a wide variety of insertion sites and target areas. Teachings of the present disclosure are not limited to power drivers and/or IO devices which may be inserted at the proximal tibia, distal tibia, humerus, or sternum.

IO access may be used as a "bridge" for temporary fluid and/or drug therapy during emergency conditions until conventional IV sites can be found and used. Conventional IV sites often become available because fluids and/or medication provided via IO access may stabilize a patient and expand veins and other portions of a patient's vascular system. IO devices and associated procedures incorporating teachings of the present disclosure may become standard care for administering medications and fluids in situations when IV access is difficult or not possible.

Intraosseous access may be used as a "routine" procedure with chronic conditions which substantially reduce or eliminate availability of conventional IV sites. Examples of such chronic conditions may include, but are not limited to, dialysis patients, patients in intensive care units and epilepsy patients. Intraosseous devices and associated apparatus incorporating teachings of the present disclosure may be quickly and safely used to provide IO access to a patient's vascular system in difficult cases such as status epilepticus to give medical personnel an opportunity to administer crucial medications and/or fluids. Further examples of such acute and chronic conditions are listed near the end of this written description.

SUMMARY OF THE DISCLOSURE

In accordance with teachings of the present disclosure, apparatus and methods are provided for gaining rapid access to a patient's vascular system. One embodiment may include a powered driver operable to insert an intraosseous device into a patient's bone marrow at a selected target site. The powered driver may include a variable speed mechanism such as a low voltage potentiometer or any other electrical device satisfactory to allow varying the speed of an associated motor.

One embodiment of the present disclosure may provide an apparatus operable to insert an intraosseous device into a bone and associated bone marrow. The apparatus may include a housing, a drive shaft, a motor, a power supply and associated electrical circuit, and a light. The drive shaft may extend from an opening in the housing and may be operable to releasably engage the intraosseous device. The motor may be disposed within the housing and rotatably engaged with the drive shaft. The power supply and associated electrical circuit may be operable to power the motor. The light may extend from the housing and be connected to the power supply and the light may be operable to illuminate an insertion site for the intraosseous device.

Another embodiment of the present disclosure may provide a powered driver operable to insert an intraosseous device into a bone and associated bone marrow. The powered driver may include a housing, a drive shaft extending from the housing, a motor, a power supply, electrical circuits, and a switch connected to the electrical circuits. The drive shaft may be operable to releasably engage the intraosseous device. The motor may be disposed within the housing and rotatably engaged with the drive shaft. The power supply and associated electrical circuit may be operable to power the motor. The switch may be operable to activate the motor to rotate the drive shaft.

Another embodiment of the present disclosure may provide an apparatus operable to insert an intraosseous device into a bone and associated bone marrow and to assist with other medical procedures. The apparatus may include a powered driver, a drive shaft, a motor, a power supply and electrical circuits, a switch, and a suction pump. The powered driver may have a housing with one end of the drive shaft extending therefrom. The one end of the drive shaft may be operable to releasably engage the intraosseous device. The motor may be disposed within the housing and rotatably engaged with the drive shaft. The power supply and electrical circuits may be operable to power the motor. The switch may be operable to activate the motor to rotate the drill shaft. The suction pump may have a connector operable to be releasably engaged with the one end of the drive shaft whereby the powered driver may operate the pump.

BRIEF DESCRIPTION OF THE DRAWINGS

A more complete and thorough understanding of the present embodiments and advantages thereof may be acquired by referring to the following description taken in conjunction with the accompanying drawings, in which like reference numbers indicate like features, and wherein:

FIG. 3A is a schematic drawing showing a powered driver disposed in a charging cradle incorporating teachings of the present disclosure;

FIG. 3B is a schematic drawing showing an isometric view of a powered driver having a battery charge indicator incorporating teachings of the present disclosure;

FIG. 3C is a schematic drawing with portions broken away showing another example of a charge indicator for a powered driver incorporating teachings of the present disclosure;

FIG. 3D is a schematic drawing with portions broken away showing still another example of a power supply status indicator for a powered driver incorporating teachings of the present disclosure;

DETAILED DESCRIPTION OF THE DISCLOSURE

Figure 1A:
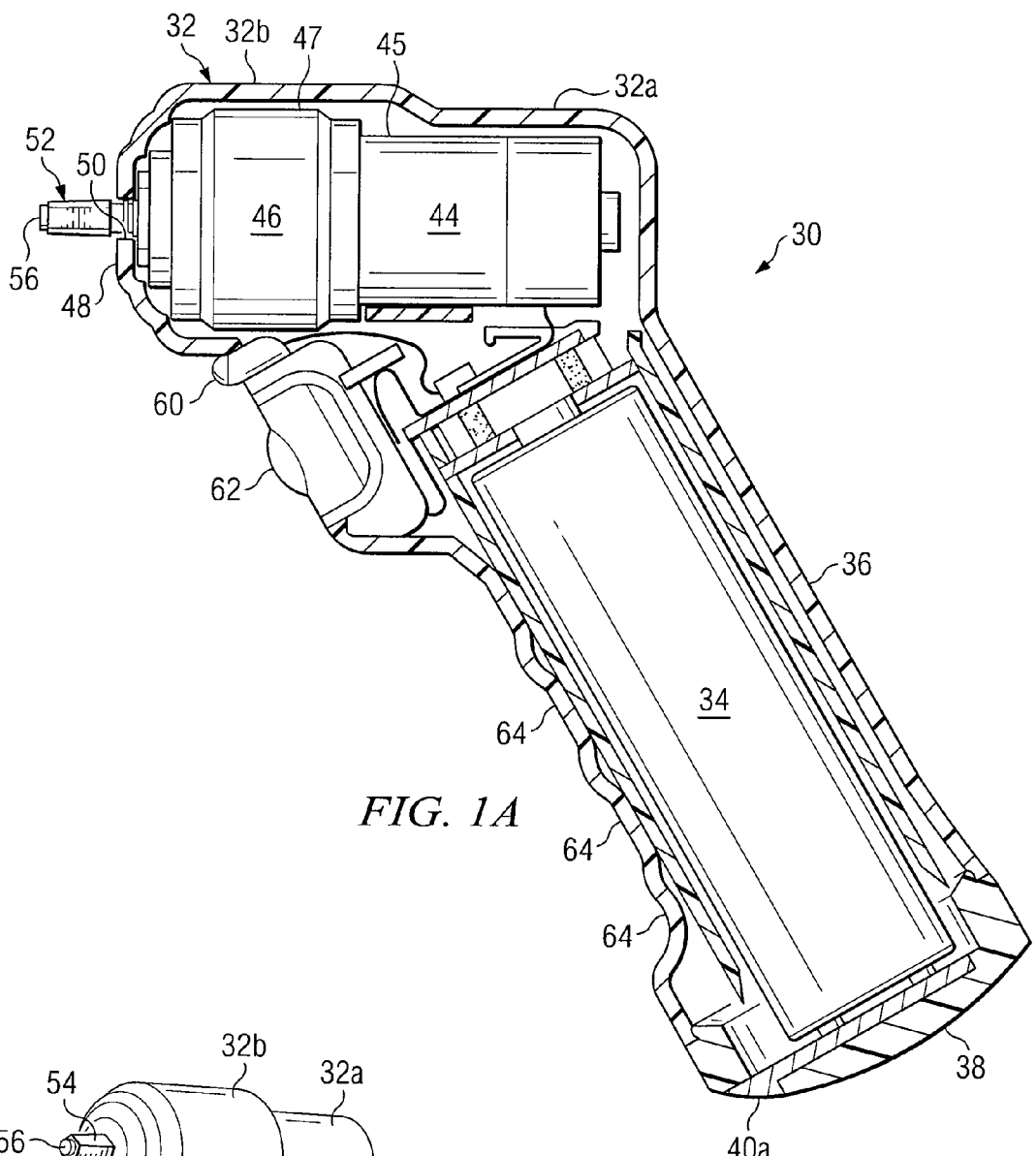
FIG. 1A is a schematic drawing in section showing one embodiment of a rechargeable powered driver incorporating teachings of the present disclosure.

Preferred embodiments of the disclosure and its advantages are best understood by reference to FIGS. 1A-10 wherein like numbers refer to same and like parts.

Apparatus and methods incorporating teachings of the present disclosure may be used to provide intraosseous access to a patient's vascular system in the sternum, the proximal humerus (the shoulder area), the proximal tibia (below the knee) and the distal tibia (above the inside of the ankle). The distal tibia may provide easier vascular access to morbidly obese patients. The distal tibia is usually a thinner area of the body. Using the distal tibia as an insertion site may allow emergency medical service personnel to pump medications and fluids into the body of obese patients when regular conventional IV access is difficult. EMS personnel may often not be able to start IVs in obese patients because their size may obscure many of the veins used for conventional IV access. Adipose tissue (fat) around normal IO access sites may be so thick that EMS personnel can't reach adjacent the bone with standard IO needles. Therefore, the distal tibia may provide an IO access site for the overweight population.

One aspect of the present disclosure may include providing a powered driver and respective IO needle sets for safe and controlled vascular access to provide medication and fluids to bone marrow, to remove biopsies of bone and/or bone marrow and to aspirate bone marrow.

Apparatus and methods incorporating teachings of the present disclosure may be used with patients of all ages and weights. For example, one IO needle set may be appropriate for patients within the weight range of 3 kilograms to 39 kilograms. A second IO needle set may be satisfactory for use with patients weighing 40 kilograms or more.

For still other applications, teeth formed on one end of a cannula or catheter may be bent radially outward to reduce the amount of time and the amount of force required to penetrate bone and associated bone marrow using the cannula or catheter. For some applications a powered driver and aspiration needle set formed in accordance with teachings of the present disclosure may provide access to a patient's bone marrow using the same amount of torque. The length of time for penetrating a relatively hard bone may be increased as compared with the length of time required to penetrate a relatively softer bone.

The circuit may limit current supplied to the motor to protect associated batteries and to protect the motor for high current flow. High current flow may correspond with high torque which indicates improper use or operation of the powered driver. High torque may also indicate that the powered driver is not driving into bone. Current flow through the motor may be directly related to torque produced by the drive shaft. For some applications the circuit may indicate when current flow through the motor is typical for penetrating the hard outer layer of a bone (compact bone issue) with an IO device. The circuit may also indicate when current flow through the motor decreases in response to the IO device penetrating associated bone marrow.

For some embodiments the powered driver may include a trigger assembly operable to activate a low speed switch, a high speed switch and/or turn an associated motor off.

For some embodiments the powered driver may include a drive shaft having one end with a generally hexagonal cross section operable to be releasably engaged with intraosseous devices including, but not limited to, biopsy needles and bone marrow aspiration needles.

For some embodiments the powered driver may include a gear assembly rotatably attached to a motor. The gear assembly may have a speed reducing ratio between 60:1 and 80:1. For some applications the gear assembly may reduce speed of rotation of an attached motor at a ratio of approximately 66:1 or 77:1.

Apparatus and methods incorporating teachings of the present disclosure may include using a first IO needle set having a fifteen (15) gage cannula with a length of approximately fifteen (15) millimeters to establish vascular access for patients weighing between approximately three (3) kilograms and thirty nine (39) kilograms. A second IO needle set having a fifteen (15) gage cannula with an approximate length of twenty-five (25) millimeters may be used to establish vascular access for patients weighing forty (40) kilograms and greater.

For some applications intraosseous needles and needle sets incorporating teachings of the present disclosure may be formed from 304-stainless steel. Standard Luer lock catheter connections may be provided on each IO needle. IO needles and needle sets incorporating teachings of the present disclosure may be easily removed from an insertion site without the use of special tooling or equipment. The reduced size and weight of drivers and IO devices incorporating teachings of the present disclosure accommodate use in emergency crash carts and emergency medical vehicles.

The term "driver" as used in this application may include any type of powered driver satisfactory for inserting an intraosseous (IO) device including, but not limited to, a penetrator assembly, catheter, IO needle, IO needle set, biopsy needle or aspiration needle into a selected portion of a patient's vascular system. Various techniques may be satisfactorily used to releasably engage or attach an IO device with a driver incorporating teachings of the present disclosure. A wide variety of connectors and associated connector receptacles, fittings and/or other types of connections with various dimensions and configurations may be satisfactorily used to releasably engage an IO device with a driver. A battery powered driver incorporating teachings of the present disclosure may be used to insert an intraosseous device into a selected target area in ten seconds or less.

The term "intraosseous (IO) device" may be used in this application to include any hollow needle, hollow drive bit, penetrator assembly, bone penetrator, catheter, cannula, trocar, inner penetrator, outer penetrator, IO needle or IO needle set operable to provide access to an intraosseous space or interior portions of a bone.

Figure 8A:
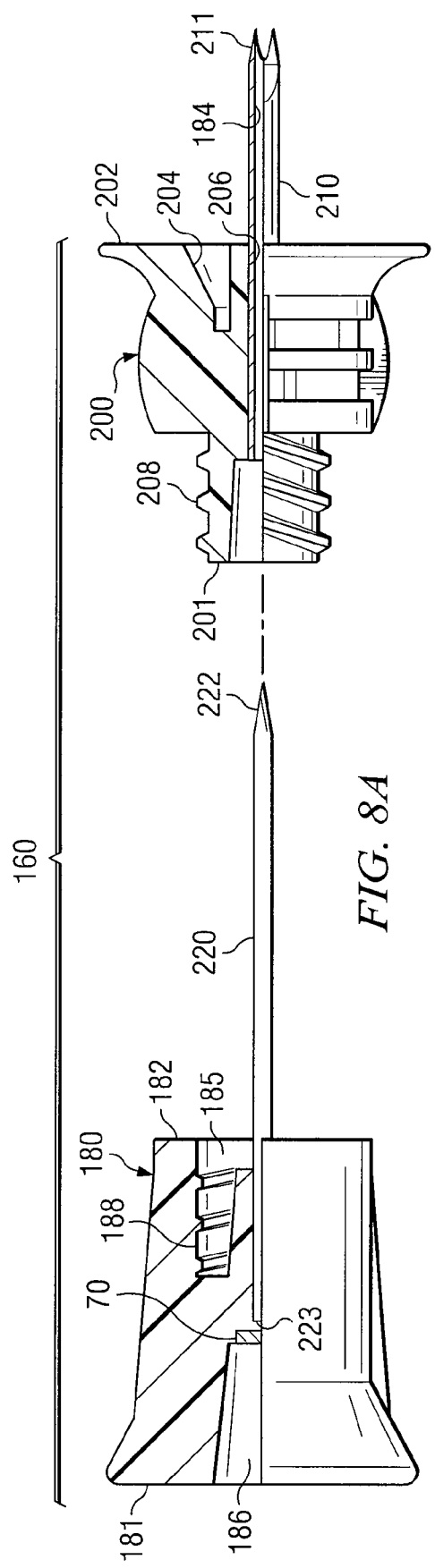
FIG. 8A is a schematic drawing showing one example of an intraosseous needle set which may be inserted into a patient's vascular system using a powered driver.
Figure 8B:
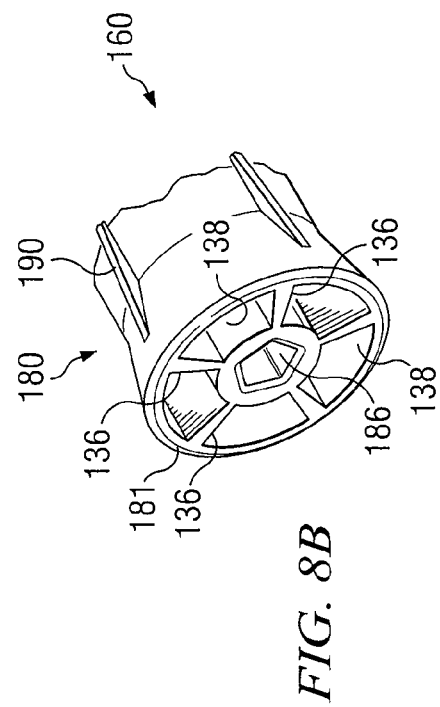
FIG. 8B is a schematic drawing showing an isometric view with portions broken away of a connector receptacle which may be releasably engaged with a powered driver incorporating teachings of the present disclosure.

For some applications an IO needle or IO needle set may include a connector with a trocar or stylet extending from a first end of the connector. A second end of the connector may be operable to be releasably engaged with a powered driver incorporating teachings of the present disclosure. An IO needle or IO needle set may also include a hub with a hollow cannula or catheter extending from a first end of the hub. A second end of the hub may include an opening sized to allow inserting the trocar through the opening and the hollow cannula. The second end of the hub may also be operable to be releasably engaged with the first end of the connector. As previously noted, the second end of the connector may be releasably engaged with a powered driver. A wide variety of connectors and hubs may be used with an IO device incorporating teaching of the present disclosure. The present disclosure is not limited to connector 180 or hub 200 as shown in FIGS. 8A and 8B.

Various features of the present disclosure may be described with respect to powered drivers 30 and 30a-30f. Various features of the present disclosure may also be described with respect to intraosseous devices such as shown in FIGS. 8A and 8B. However, the present disclosure is not limited to use with intraosseous device 160 or powered drivers 30 and 30a-30f.

Figure 1B:
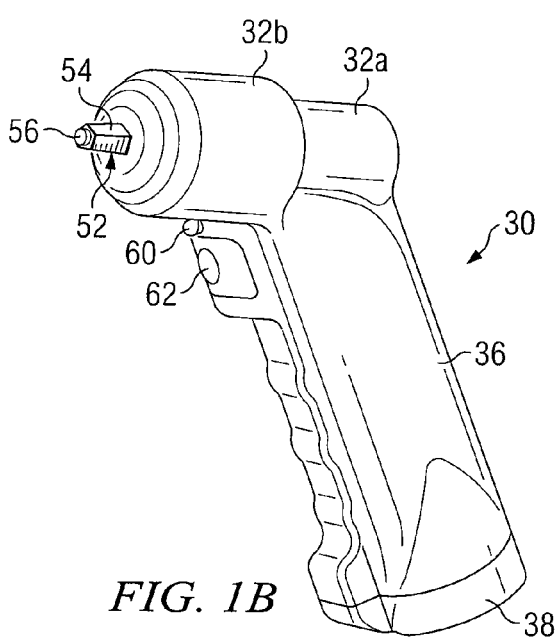
FIG. 1B is a schematic drawing showing an isometric view of the rechargeable powered driver of FIG. 1A.

Powered driver 30 as shown in FIGS. 1A, 1B and 3A may be satisfactorily used to insert an intraosseous device at a desired insertion site adjacent to a bone and associated bone marrow (not expressly shown). For embodiments such as shown in FIGS. 1A, 1B and 3A powered driver 30 may include one or more features of the present disclosure including, but not limited to, a light operable to illuminate an insertion site, charging contacts and associated charging circuitry, a power supply status indicator, trigger guard, variable speed controller, safety switch and/or timing circuit. At least one or more of the preceding features and/or additional features of the present disclosure may also be shown with respect to powered drivers 30-30f and/or 330a-330k.

Various components associated with powered driver 30 may be disposed within housing 32. For example a power source such as rechargeable battery pack 34 may be disposed within handle 36. Battery pack 34 may have various configurations and may include multiple batteries disposed within sealed packaging material. For other applications, a non-rechargeable battery pack may also be disposed within handle 36.

Handle 36 may be generally described as an elongated, hollow container sized to receive battery pack or power supply 34. Cap 38 may be disposed on one end of handle 36. Cap 38 may be removed to allow inserting and removing battery pack 34 therefrom. Handle 36 may also include finger grips 64 having generally ergonomic configurations.

For embodiments such as shown in FIGS. 1A, 1B and 3A cap 38 may include a pair of charging contacts 40a and 40b. A portion of each contact 40a and 40b may extend from cap 38 for engagement with an appropriate charging receptacle. See FIG. 3A. For some applications cap 38 and adjacent portions of handle 36 may have heavy duty screw on or thread connections (not expressly shown). For some applications cap 38 may be formed from relatively strong, heavy duty polymeric material.

Motor 44 and gear assembly 46 may also be disposed within portions of housing 32 adjacent to handle 36. For embodiments represented by powered drivers 30-30e and 330a-330k, motor 44 and gear assembly 46 may be generally aligned with each other. Motor 44 may be connected with one end of gear assembly 46. Drive shaft 52 may be engaged with and extend from another end of gear assembly 46 opposite from motor 44.

For some applications both motor 44 and gear assembly 46 may have generally cylindrical configurations. Exterior portion 45 of motor 44 may correspond with the largest nominal outside diameter associated with motor 44. Exterior portion 47 of gear assembly 46 may correspond with the largest nominal outside diameter associated with gear assembly 46. For embodiments of the present disclosure represented by powered drivers 30-30e and 330a-330k, exterior portion 47 of gear assembly 46 may represent a nominal outside diameter portion larger than any other outside diameter portion associated with motor 44. In other embodiments of the present disclosure represented by powered driver 330i, exterior portion 47 of gear assembly 46 may be smaller than outside diameter portions associated with impact device 44a.

Portions of housing 32 may have generally similar cylindrical configurations corresponding with exterior portions of motor 44 and gear assembly 46. For example, segment 32a of housing 32 may have a generally cylindrical, hollow configuration with an inside diameter compatible with exterior portion 45 of motor 44. Housing segment 32b may have a generally cylindrical, hollow configuration with an inside diameter compatible with exterior portion 47 of gear assembly 46. Since portions of gear assembly 46 have an outside diameter that is larger than the outside diameter of motor 44, housing segment 32b may have a larger outside diameter than the outside diameter of housing segment 32a.

Motors and gear assemblies satisfactory for use with a powered driver incorporating teachings of the present disclosure may be obtained from various vendors. Such motor and gear assemblies are typically ordered as "sets" with one end of each motor securely attached to an adjacent end of an associated gear assembly. The gear assemblies may sometimes be referred to as "reduction gears" or "planetary gears".

A drive shaft having desired dimensions and configuration may extend from the gear assembly opposite from the motor. The drive shaft may be provided as part of each motor and gear assembly set. The dimensions and/or configuration of an associated housing may be modified in accordance with teachings of the present disclosure to accommodate various types of motors, gear assemblies and/or drive shafts. For example, powered drivers used with aspiration needles and/or biopsy needles may include gear assemblies with larger dimensions required to accommodate larger speed reduction ratios, for example between 60:1 and 80:1, resulting in slower drive shaft RPM. Powered drivers used to provide intraosseous access during emergency medical procedures may operate at a higher speed and may include gear assemblies having a smaller speed reduction ratio, for example between 10:1 and 30:1, resulting in higher drive shaft RPM. For some applications, the difference in size for gear assemblies may result in increasing the inside diameter of an associated housing by approximately two to three millimeters to accommodate larger gear assemblies associated with powered drivers used to insert biopsy needles and/or aspiration needles.

Distal end or first end 48 of housing 32 may include opening 50 with portions of drive shaft 52 extending therefrom. For some applications the portion of drive shaft 52 extending from housing 32 may have a generally pentagonal shaped cross section with tapered surfaces 54 disposed thereon. Tapered surfaces 54 may be disposed at an angle of approximately three (3°) degrees with respect to a longitudinal axis or rotational axis (not expressly shown) associated with drive shaft 52. Relatively small magnet 56 disposed on the extreme end of drive shaft 52 opposite from housing 32. Fittings and/or connectors with various dimensions and/or configurations other than drive shaft 52 and/or magnet 56 may also be satisfactorily used with a powered driver incorporating teachings of the present disclosure.

Figure 9A:
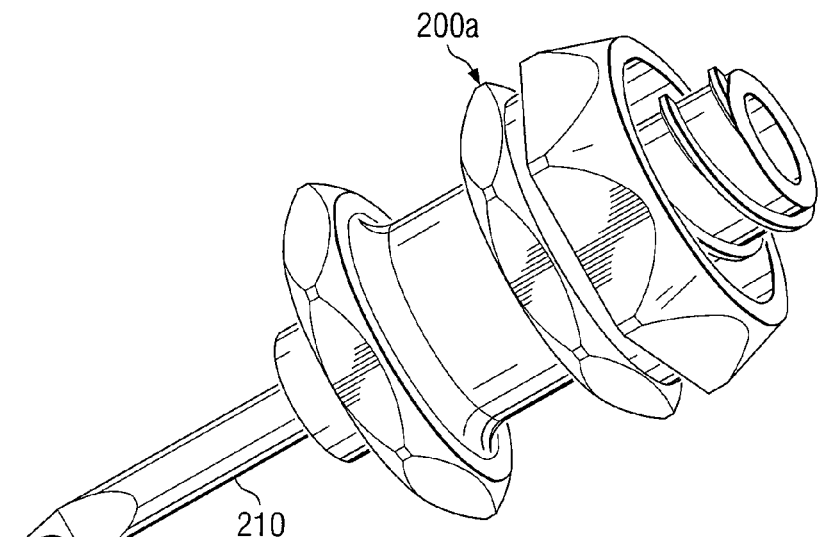
FIG. 9A is a schematic drawing showing an isometric view of one embodiment of a hub which may be installed by a powered driver in accordance with teachings of the present disclosure.
Figure 9B:
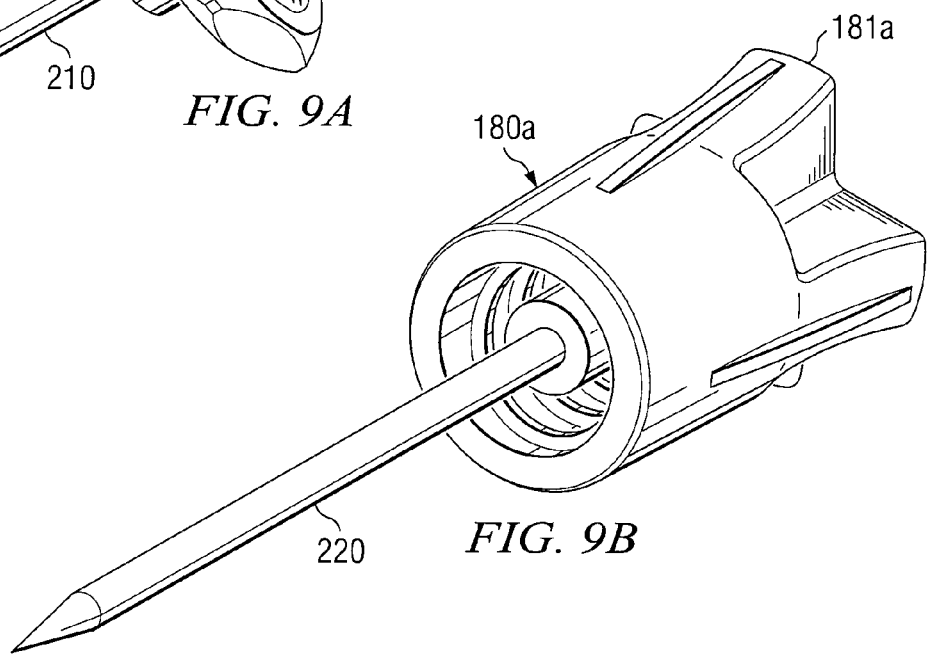
FIG. 9B is a schematic drawing showing an isometric view of one embodiment of a connector which may be installed by a powered driver in accordance with teachings of the present disclosure.
Figure 10:
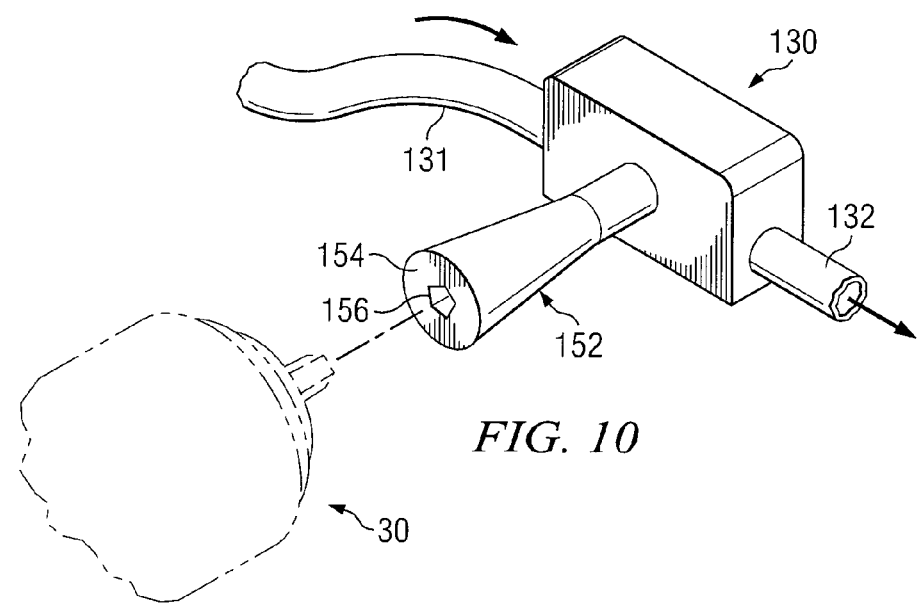
FIG. 10 is a schematic drawing showing an isometric view with portions broken away of a pump which may be operated by a powered driver in accordance with teachings of the present disclosure.

Intraosseous devices having corresponding tapered openings or connector receptacles may be releasably engaged with portions of drive shaft 52 extending from housing 32. For example, portions of drive shaft 52 extending from distal end 48 may be releasably engaged with tapered opening 186 in connector 180 as shown in FIGS. 8A and 8B or tapered opening 156 in connector receptacle 152 as shown in FIGS. 9 and 10.

For embodiments such as shown in FIGS. 1A, 1B and 3A, powered driver 30 may also include light 60 disposed adjacent to trigger assembly 62. Electrical circuits and associated wiring contacts may also be disposed within housing 32 to supply electrical power to light 60. Trigger assembly 62 may be used to activate electrical circuits to provide electricity from rechargeable battery 34 to motor 44 and/or light 60. A block diagram showing one example of such electrical circuits is shown in FIG. 2A.

Figure 2A:
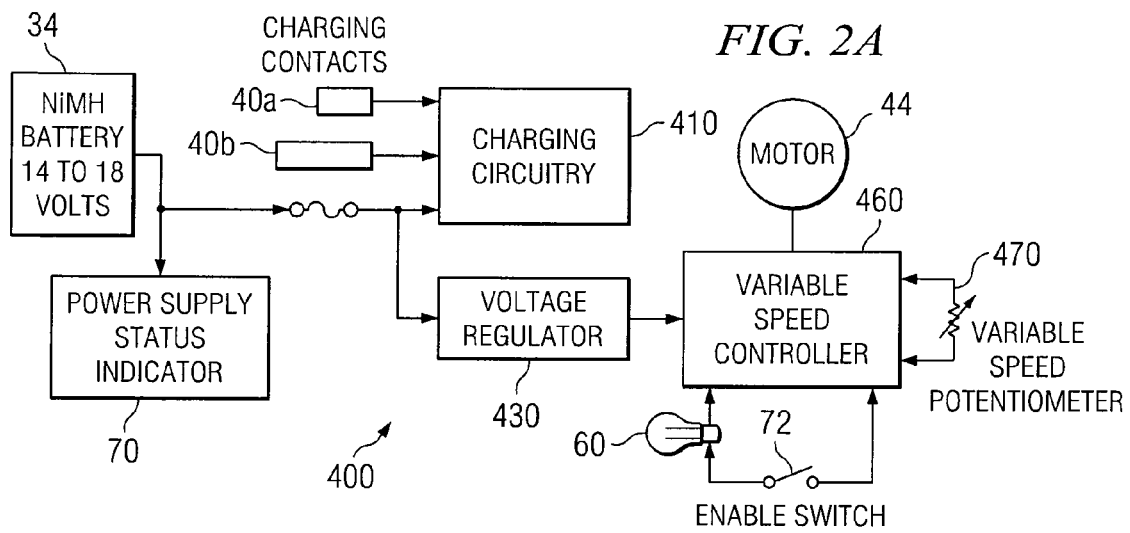
FIG. 2A is a schematic drawing showing one example of an electrical power circuit incorporating teachings of the present disclosure.

A block diagram showing one example of electrical circuits and other components which may be satisfactory used with a powered driver incorporating teachings of the present disclosure is shown in FIG. 2A. Various features of the present disclosure may be described with respect to electrical system 400 as shown in FIG. 2A. Electrical system 400 may include various components such as power supply or battery pack 34, charging contacts 40a and 40b, motor 44, light 60 and/or enable switch 62. Electrical system 400 may include a wide variety of electrical circuits and electrical components including, but not limited to, power supply status indicator 70 and electrical charging circuit 410, voltage regulator 430 and variable speed controller 460. As previously noted, power supply or battery pack 34 may include one or more rechargeable batteries. Various types of nickel metal hydride (NiMH) batteries may be used (particularly lithium batteries). Battery pack 34 may supply fourteen (14) to eighteen (18) volts of direct current (DC) power. However, a wide variety of chargeable and non-rechargeable batteries may be satisfactorily used with powered drivers incorporating teachings of the present disclosure.

A wide variety of electrical circuits and/or electronic indicators may be used with power supply status indicator 70. Additional information concerning such electrical circuits and displays may be described with respect to various power supply status indicators as shown in FIGS. 3B, 3C and 3D.

Figure 2B:
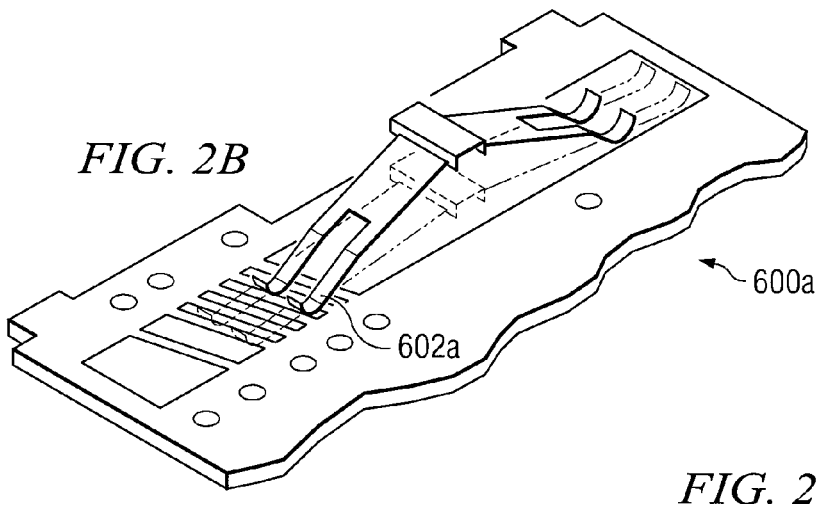
FIG. 2B is a schematic drawing showing an example of one component of a variable speed controller satisfactory for use with a powered driver in accordance with teachings of the present disclosure.
Figure 2C:
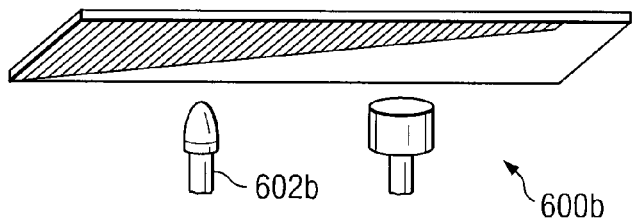
FIG. 2C is an isometric drawing showing an example of another component of a variable speed controller which may be used with a powered driver in accordance with teachings of the present disclosure.
Figure 2D:
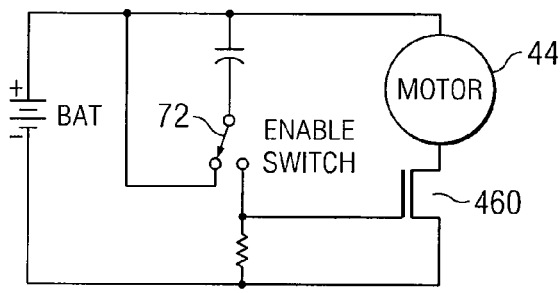
FIG. 2D is a schematic drawing showing an example of an electrical power circuit having an enable switch or safety switch incorporating teachings of the present disclosure.

A wide variety of charging circuits, voltage regulators and variable speed controllers may be satisfactorily used with a powered driver incorporating teachings of the present disclosure. Various examples of such charging circuits, voltage regulators and/or variable speed controllers are shown in FIGS. 2B and 2C. Various types of commercial available charging circuits, voltage regulators and/or variable speed controllers may be satisfactorily used with a powered driver incorporating teachings of the present disclosure. Various examples of commercially available microcontrollers may be satisfactory for use with variable speed controller 460. Variable resistor 600a as shown in FIG. 2B and variable resistor 600b as shown in FIG. 2C represents examples of mechanical devices having slidable contacts which may be used to vary current supplied to motor 44. A trigger assembly incorporating teachings of the present disclosure may be satisfactory used to move one or more of the electrical contacts 602a or 602b.

Figure 5A:
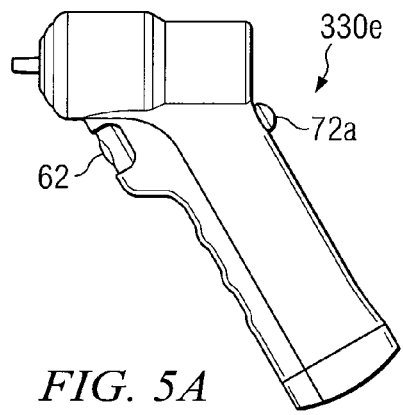
FIG. 5A is a schematic drawing showing an isometric view of a powered driver having a safety switch incorporating teachings of the present disclosure.
Figure 5B:
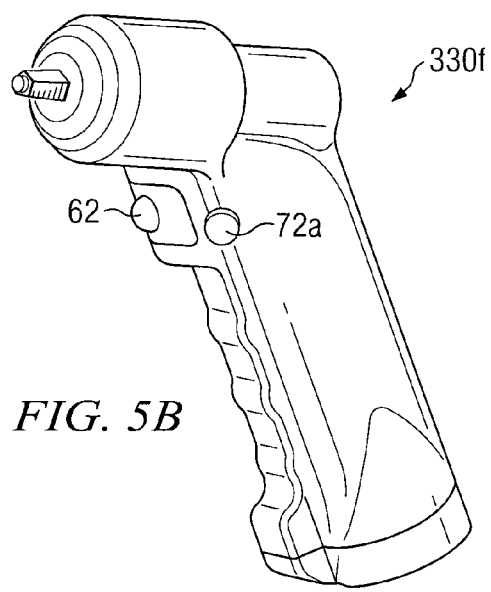
FIG. 5B is a schematic drawing showing an isometric view of another powered driver having an enable switch incorporating teachings of the present disclosure.
Figure 5C:
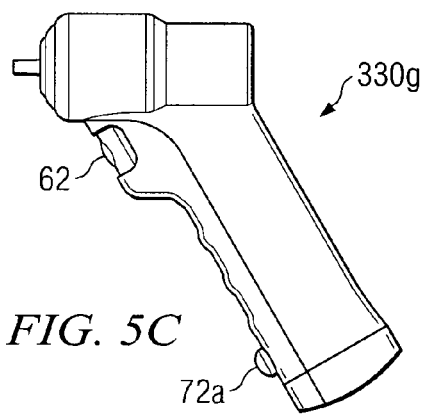
FIG. 5C is a schematic drawing showing an isometric view of still another powered driver having a safety switch incorporating teachings of the present disclosure.

Switch 62 may be provided to prevent inadvertent or undesired activation of motor 44. Switch 62 may prevent discharge of battery 34 when an associated powered device is carried in a backpack and/or mobile storage container. An associated button 72a may be disposed on exterior portions of a housing to activate the variable speed controller 460. Button 72a may be located at various positions on the exterior of a housing associated with a powered driver incorporating teachings of the present disclosure as shown in FIGS. 5A-5C. A wide variety of indicators including, but not limited to, light emitting diodes (LED), liquid crystal displays (LCD) and small more conventional light bulbs may be satisfactorily used with a powered driver according to teachings of the present disclosure.

FIG. 3A shows one example of a cradle which may be used to recharge a powered driver in accordance with teachings of the present disclosure. Cradles and/or holders incorporating teachings of the present disclosure may be fabricated from a wide variety of thermoplastic and/or polymeric materials including, but not limited to, polycarbonates. Such materials may be filled with glass fibers or any other fibers satisfactory for use in forming a cradle or holder operable to hold and/or recharge a powered driver in accordance with teachings of the present disclosure. Nylon filled with glass may be used for some applications.

Materials used to form cradle 280 may be relatively low cost but durable. Such materials may be relatively stiff to secure a powered driver therein and may also flex without breaking to allow inserting and removing a powered driver at least five hundred (500) times.

Cradle 280 may have a length and width selected to be compatible with exterior portions of housing 32 and corresponding dimensions of powered driver 30. For some applications first end 281 and second end 282 may have generally rounded configurations. A notch (not expressly shown) may also be formed in first end 281 to accommodate portions of drive shaft 52. Various types of holders, clamps or quick release mechanisms may be included as part of cradle 280. For embodiments such as shown in FIG. 3A, cradle 280 may include a pair of arms 284 projecting from respective edges of cradle 280. Only one arm 284 is shown in FIG. 3A.

Arms 284 may be relatively strong with sufficient flexibility to allow inserting and removing portions of powered driver 30 from engagement with cradle 280. The height of arms 284 relative to adjacent longitudinal edges of cradle 280 may be based at least in part on the corresponding dimensions of handle 36 and other portions of housing 32. The spacing or gap formed between arms 284 may be selected to accommodate the width of handle 36. Respective rib 286 may be formed on the end of each arm 284. The configuration of ribs 286 may be selected to be compatible with a snug but releasable snap fit with adjacent portions of handle 36.

For some applications walls or partitions 290 may be formed adjacent to respective arms 294. Only one wall 290 is shown in FIG. 3A. Partitions or walls 290 may be spaced from each other a sufficient distance to accommodate associated portions of housing 32 and may be sized to prevent accidental activation of trigger assembly 62.

End 282 of cradle 280 may be modified to include electrical contact (not expressly shown) operable to engage recharging contacts 40a and 40b. Electric power cable 292 may also extend from end 282. Electrical power cable 292 may be inserted into an appropriate electrical outlet for use in recharging powered driver 30. A plurality of lights 296, 298 and 300 may be provided on exterior portions of cradle 300 to indicate the status of rechargeable battery 34. For example light 296 may indicate red when rechargeable battery 34 is discharged below a desired level. Light 298 may be flashing yellow to indicate that rechargeable battery 34 is being recharged and/or discharged. Light 300 may be steady green to indicate when rechargeable battery 34 has been fully recharged. Lights 296, 298 and 300 may also alternately blink or have a steady state condition.

Powered drive 30a as shown in FIG. 3B may include an indicator operable to indicate the status of a power supply disposed within handle 36. For some embodiments status indicator 70a may be disposed at proximal end or second end 49a of powered driver 30a. A digital display indicating the number of insertions available from a power supply disposed within housing 32a may be provided by indicator 70 at proximal end 49a of housing 32a. The power supply may be any type of battery or other suitable source of power.

An embodiment of the present disclosure is shown in FIG. 3C which includes status indicator 70b disposed on second end or proximal end 49b of powered driver 30b. Status indicator 70b may include digital indication 72 showing the number of insertions remaining in an associated power source. In addition variable indicator scale 74 may be provided to show the status of an associated power source between fully charged and recharge required. For example, variable indicator scale 74 may include a voltmeter, an amp meter, and/or any other component operable to measure the status of an associated power supply. As another example, variable indicator scale 74 may be calibrated to display a percentage of full charge and/or a number of insertions remaining.

A further embodiment of the present disclosure is shown in FIG. 3D. For this embodiment lights 296, 298 and 300 may be disposed on proximal end or second end 49c of powered driver 30c. Lights 296, 298 and 300 may function as previously describe with respect to cradle 280.

Figure 7A:
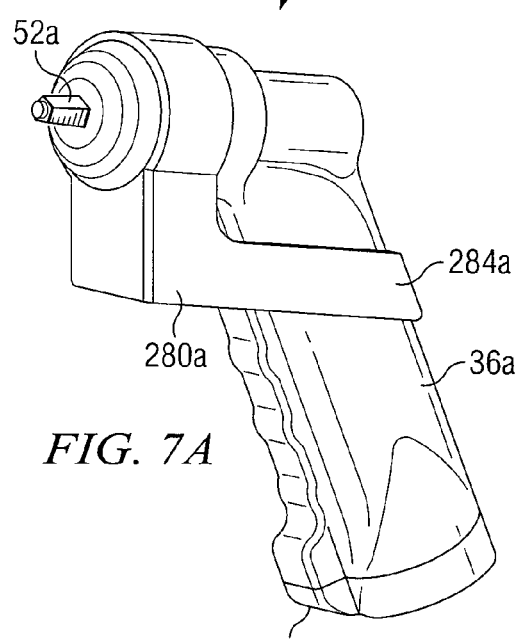
FIG. 7A is a schematic drawing showing a wall mounted cradle for a powered driver incorporating teachings of the present disclosure.
Figure 7B:
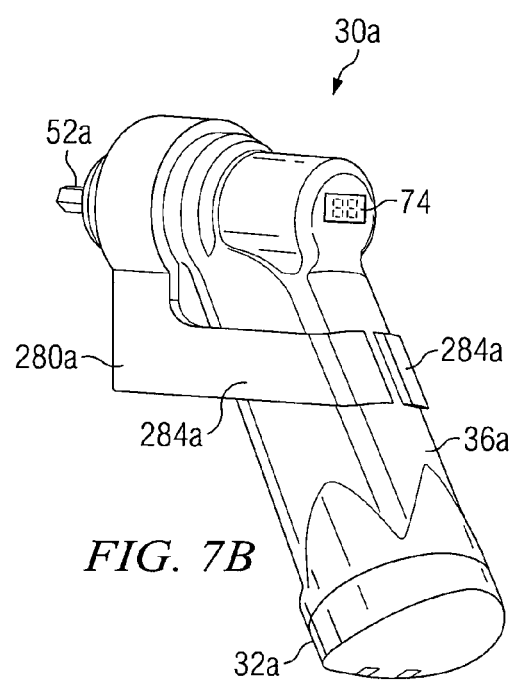
FIG. 7B is a schematic drawing showing another isometric view of a cradle and powered driver of FIG. 7B.

FIGS. 7A and 7B show another embodiment of the present disclosure including powered driver 330j disposed within cradle 280a. Cradle 280a may include arms 284a as described in relation to FIG. 3b. Arms 284a may be relatively strong with sufficient flexibility to allow inserting and removing portions of powered driver 330j from engagement with cradle 280a. The height of arms 284a relative to adjacent longitudinal edges of cradle 280a may be based at least in part on the corresponding dimensions of handle 336 and other portions of housing 332. The spacing or gap formed between arms 284 may be selected to accommodate the width of handle 336.

Figure 4A:
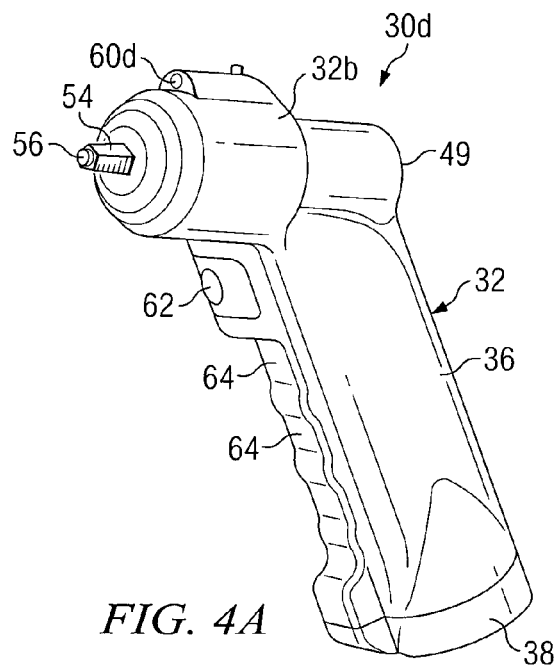
FIG. 4A is a schematic drawing showing an isometric view of a powered driver having a light in accordance with teachings of the present disclosure.
Figure 4B:
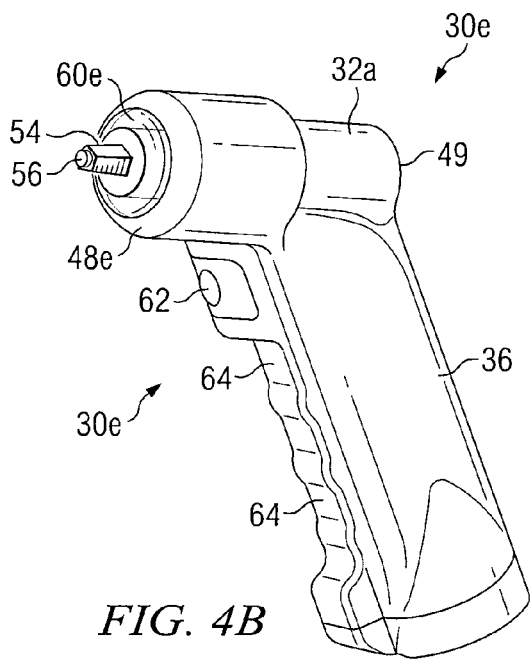
FIG. 4B is a schematic drawing showing an isometric view of another example of a light disposed on a powered driver in accordance with teachings of the present disclosure.

Powered drivers 30d and 30e as shown in FIGS. 4A and 4B show alternative locations for a light disposed on a powered driver in accordance with teachings of the present disclosure. Powered driver 30d may include substantially the same features as powered driver 30 except light 60d may be disposed on housing segment 32b opposite from trigger assembly 62. For embodiments such as shown in FIG. 4B light 60e may be disposed on distal end or first end 48e of powered driver 30e. Light 60e may extend approximately three hundred sixty degrees (360°) around the perimeter of associated drive shaft 54.

Figure 4C:
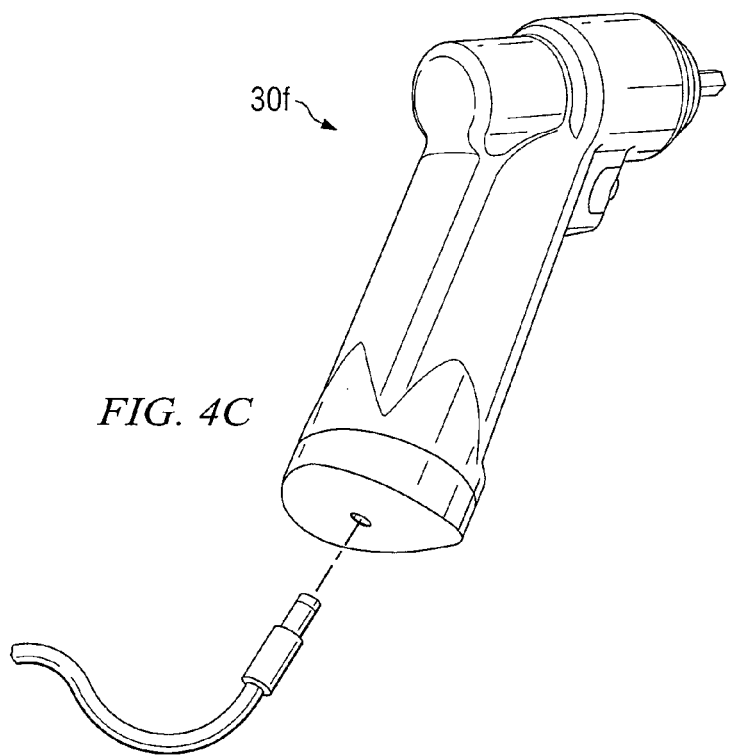
FIG. 4C is a schematic drawing showing another example of a rechargeable powered driver incorporating teachings of the present disclosure.

A further embodiment of a rechargeable powered driver incorporating teachings of the present disclosure is shown in FIG. 4C. For embodiments represented by powered driver 30f, cap 38f may be disposed on one end of handle 36. Cap 38 may include opening 40 sized to receive charging connection 130 attached to power cable 132. A wide variety of recharging connectors may be used to provide power to cable 132.

Figure 6A:
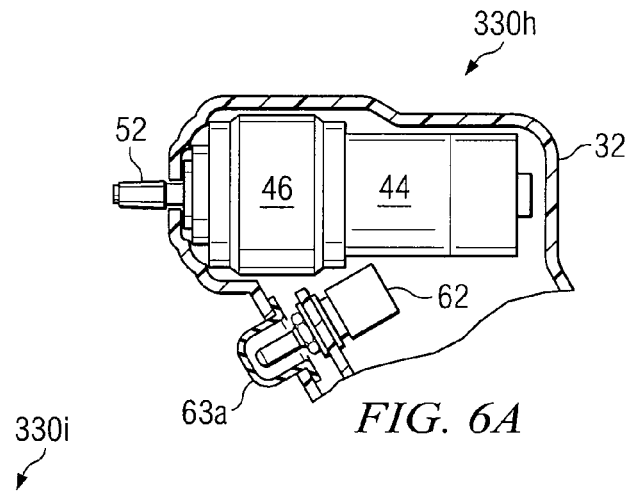
FIG. 6A is a schematic drawing in section with portions broken away showing one example of a protective covering for a trigger assembly or switch assembly of a powered driver incorporating teachings of the present disclosure.
Figure 6B:
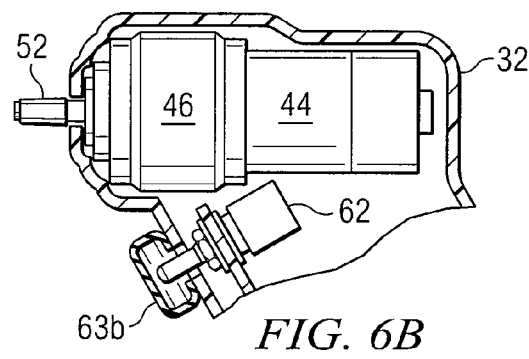
FIG. 6B is a schematic drawing showing another example of a protective cover for a trigger assembly or switch assembly of a powered driver incorporating teachings of the present disclosure.

FIGS. 6A and 6B show examples of a protective covering 63 for trigger assembly 62 or switch assembly 62 of powered driver incorporating teachings of the present disclosure. Housing 32 may be sealed to prevent blood, other bodily fluids, and/or other contaminants from reaching interior portions of housing 32 and components disposed therein (e.g., battery 34, motor 44, and/or gear assembly 46). FIGS. 6A and 6B show protective covering 63a and 63b configured to seal with housing 32. Protective covering 63a and 63b may be formed with an elastomeric material chosen for resistance to wear, electrical current, impermeability, and/or any other characteristic sought as long as it allows operation of switch assembly 62 by the user.

Figure 6C:
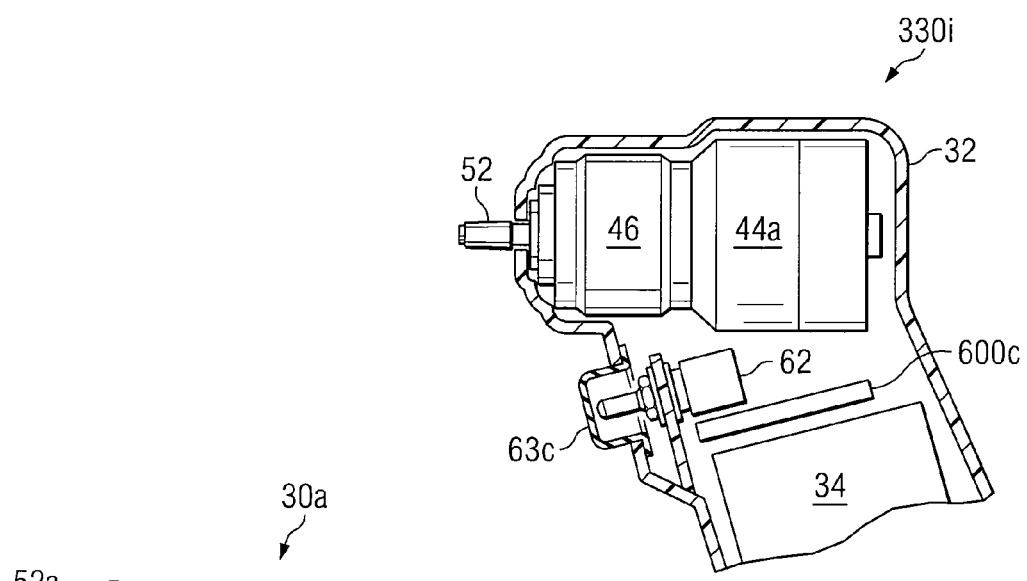
FIG. 6C is an isometric drawing showing a cross-section of a powered driver incorporating teachings of the present disclosure.

FIG. 6C shows powered driver 330i incorporating an impact device 44a associated with gearbox 46 and power sensor circuit 600c. Impact device 44a may be configured to operate in a similar manner to an impact wrench by storing energy in a rotating mass then delivering it suddenly to gearbox 46. In some embodiments, impact device 44a will require less total power from power supply 34.

Power sensor circuit 600c may detect current changes between impact device 44a and power supply 34. In some applications, current changes between impact device 44a and power supply 34 may indicate bone penetration is complete. Power sensor circuit 600c may be operable to automatically reduce or cut power from power supply 34 to impact device 44a once the associated intraosseous device has penetrated the cortex of the bone.

An intraosseous device (IO), sometimes referred to as a penetrator assembly or IO needle set, may include an outer penetrator such as a cannula, needle or hollow drive bit which may be of various sizes. Needles may be small (for pediatric patients), medium (for adults) and large (for oversized adults). Penetrator, cannulas or needles may be provided in various configurations depending on the clinical purpose for needle insertion. For example, there may be one configuration for administering drugs and fluids and an alternate configuration for sampling bone marrow or for other diagnostic purposes although one needle configuration may be suitable for both purposes. Needle configuration may vary depending on the site chosen for insertion of a needle.

A wide variety of trocars, spindles and/or shafts may be disposed within a catheter or cannula during insertion at a selected insertion site. Such trocars, spindles and shafts may also be characterized as inner penetrators. A catheter, cannula, hollow needle or hollow drive bit may sometimes be characterized as an outer penetrator.

For some applications a layer or coating (not expressly shown) of an anticoagulant such as, but not limited to, heparin may be placed on interior and/or exterior portions of a catheter or cannula to prevent thrombotic occlusion of the catheter or cannula. Anticoagulants may reduce platelet adhesion to interior surfaces of the catheter or cannula and may reduce clotting time of blood flowing into and through the catheter or cannula. Placing a layer of an anticoagulant on exterior portions of a catheter or cannula adjacent to an associated tip and/or side ports may be helpful to prevent clotting.

Penetrator assembly 160 as shown in FIGS. 8A and 8B may include connector 180, and associated hub 200, outer penetrator 210 and inner penetrator 220. Penetrator assembly 160 may include an outer penetrator such as a cannula, hollow tube or hollow drive bit and an inner penetrator such as a stylet or trocar. Various types of stylets and/or trocars may be disposed within an outer penetrator. For some applications outer penetrator or cannula 210 may be described as a generally elongated tube sized to receive inner penetrator or stylet 220 therein. Portions of inner penetrator 220 may be disposed within longitudinal passageway 184 extending through outer penetrator 210. The outside diameter of inner penetrator 220 and the inside diameter of longitudinal passageway 184 may be selected such that inner penetrator 220 may be slidably disposed within outer penetrator 210.

Metallic disc 170 may be disposed within opening 186 for use in releasably attaching connector 180 with magnet 56 disposed on the end of drive shaft 52. End 223 of inner penetrator 220 is preferably spaced from metallic disc 170 with insulating or electrically nonconductive material disposed therebetween.

Tip 211 of outer penetrator 210 and/or tip 222 of inner penetrator 220 may be operable to penetrate bone and associated bone marrow. The configuration of tips 211 and/or 222 may be selected to penetrate a bone or other body cavities with minimal trauma. First end or tip 222 of inner penetrator 220 may be trapezoid shaped and may include one or more cutting surfaces. In one embodiment outer penetrator 210 and inner penetrator 220 may be ground together as one unit during an associated manufacturing process. Providing a matching fit allows respective tips 211 and 222 to act as a single driving unit which facilitates insertion and minimizes damage as portions of penetrator assembly 160 are inserted into a bone and associated bone marrow. Outer penetrator 210 and/or inner penetrator 220 may be formed from stainless steel, titanium or other materials of suitable strength and durability to penetrate bone.

Hub 200 may be used to stabilize penetrator assembly 160 during insertion of an associated penetrator into a patient's skin, soft tissue and adjacent bone at a selected insertion site. First end 201 of hub 200 may be operable for releasable engagement or attachment with associated connector 180. Second end 202 of hub 200 may have a size and configuration compatible with an associated insertion site for outer penetrator 210. The combination of hub 200 with outer penetrator 210 may sometimes be referred to as a "penetrator set" or intraosseous needle.

Connector 180 and attached inner penetrator 220 may be releasably engaged with each other by Luer type fittings, threaded connections or other suitable fittings formed on first end 201 of hub 200. Outer penetrator 210 extends from second end 202 of hub 200.

For some applications connector 180 may be described as a generally cylindrical tube defined in part by first end 181 and second end 182. The exterior of connector 180 may include an enlarged tapered portion adjacent to end 181. A plurality of longitudinal ridges 190 may be formed on the exterior of connector 180 to allow an operator to grasp associated penetrator assembly 160 during attachment with a drive shaft. See FIG. 1A. Longitudinal ridges 190 also allow connector 180 to be grasped for disengagement from hub 200 when outer penetrator 210 has been inserted into a bone and associated bone marrow.

Second end 182 of connector 180 may include opening 185 sized to receive first end 201 of hub 200 therein. Threads 188 may be formed in opening 185 adjacent to second end 182 of connector 180. Threaded fitting 188 may be used in releasably attaching connector 180 with threaded fitting 208 adjacent to first end 201 of hub 200.

First end 201 of hub 200 may include a threaded connector 208 or other suitable fittings formed on the exterior thereof. First end 201 may have a generally cylindrical pin type configuration compatible with releasably engaging second end or box end 182 of connector 180.

For some applications end 202 of hub 200 may have the general configuration of a flange. Angular slot or groove 204 sized to receive one end of protective cover or needle cap 234 may be formed in end 202. Slot or groove 204 may be used to releasable engage a needle cover (not expressly shown) with penetrator assembly 160.

For some applications a penetrator assembly may include only a single, hollow penetrator. For other applications a penetrator assembly may include an outer penetrator such as a cannula, hollow needle or hollow drive bit and an inner penetrator such as a stylet, trocar or other removable device disposed within the outer penetrator. Penetrator 210 is one example of a single, hollow penetrator.

The size of a penetrator may vary depending upon the intended application for the associated penetrator assembly. Penetrators may be relatively small for pediatric patients, medium size for adults and large for oversize adults. By way of example, a penetrator may range in length from five (5) mm to thirty (30) mm. The diameter of a penetrator may range from eighteen (18) gauge to ten (10) gauge. The length and diameter of the penetrator used in a particular application may depend on the size of a bone to which the apparatus may be applied. Penetrators may be provided in a wide variety of configurations depending upon intended clinical purposes for insertion of the associated penetrator. For example, there may be one configuration for administering drugs and/or fluids to a patient's bone marrow and an alternative configuration for sampling bone marrow and/or blood from a patient. Other configurations may be appropriate for bone and/or tissue biopsy.

For some applications connector 180 may be described as having a generally cylindrical configuration defined in part by first end 181 and second end 182. SEE FIG. 2B. Exterior portions of connector 180 may include an enlarged tapered portion adjacent to end 181. A plurality of longitudinal ridges 190 may be formed on the exterior of connector 180 to allow an operator to grasp associated penetrator assembly 160 during attachment with a drive shaft. Longitudinal ridges 190 also allow connector 180 to be grasped for disengagement from hub 200 when outer penetrator 210 has been inserted into a bone and associated bone marrow.

First end 181 of connector 180 may include opening 186 sized to receive portions drive shaft 52 therein. A plurality of webs 136 may extend radially outward from connector receptacle 186. Webs 136 cooperate with each other to form a plurality of openings 138 adjacent to first end 181. Opening 186 and openings 138 cooperate with each other to form portions of a connector receptacle operable to receive respective portions of connector 30 therein. FIGS. 9A and 9B show isometric views of embodiments of connector 180a and hub 200a.

A wide variety of accessory tools and devices are frequently carried by emergency medical service personnel and/or first responders. Pump assembly 130 as shown in FIG. 10 represents an example of an accessory tool which may be operated by a powered driver incorporating teachings of the present disclosure. Pump assembly 130 may include housing 134 with connector receptacle 152 extending therefrom. Various components of pump assembly 130 (not expressly shown) may be disposed within housing 134 and rotatably attached with connector receptacle 152. Inlet tubing 131 may be provided to communicate fluids with interior portions of pump housing 134. Outlet tubing 132 may be provided to direct fluids exiting from pump assembly 130. Such fluids may be various types of liquids associated with medical procedures. Such fluids may include small particulate matter. Pump assembly 130 may sometimes function as a vacuum or suction pump for such procedures.

First end 154 of connector receptacle 152 may include opening 156 similar to opening 186 as described with respect to connector 180. End 252 extending from power driver 230a may be disposed within opening 156 to rotate connector receptacle 152 and attached components of pump assembly 130a. As a result, powered driver 230a may be used to pump fluids from inlet 131 through pump assembly 130a and outwardly from outlet 132.

Examples of acute and chronic conditions which may be treated using powered drivers, intraosseous devices, and procedures incorporating teachings of the present disclosure include, but are not limited to, the following:
 Anaphylaxis (epinephrine, steroids, antihistamines, fluids, and life support)
 Arrhythmia (anti-arrhythmics, electrolyte balance, life support);
 Burns (fluid replacement, antibiotics, morphine for pain control);
 Cardiac arrest (epinephrine, atropine, amiodarone, calcium, xylocaine, magnesium);
 Congestive heart failure (life support, diuretics, morphine, nitroglycerin);
 Dehydration (emergency port for life support, antibiotics, blood, electrolytes);
 Diabetic Ketoacidosis (life support, electrolyte control, fluid replacement);
 Dialysis (emergency port for life support, antibiotics, blood, electrolytes);
 Drug overdose (naloxone, life support, electrolyte correction);
 Emphysema (life support, beta adrenergics, steroids);
 Hemophiliacs (life support, blood, fibrin products, analgesics);
 Osteomyelitis (antibiotics directly into the site of infection, analgesics);
 Pediatric applications (shock, dehydration, nutrition, electrolyte correction);
 Renal Failure (both acute and chronic kidney failure, inability to purify blood);
 Seizures (anti-seizure medications, life support, fluid balance);
 Shock (life support fluids, pressor agents, antibiotics, steroids);
 Sickle cell crisis (fluid, morphine for pain, blood, antibiotics); and
 Trauma (emergency port for life support fluids, antibiotics, blood, electrolytes).

Although the present disclosure and its advantages have been described in detail, it should be understood that various changes, substitutions and alternations can be made herein without departing from the spirit and scope of the disclosure as defined by the following claims.

What is claimed is:

1. A powered driver operable to insert an intraosseous device into a bone and associated bone marrow comprising:
   a housing having one end of a rotatable drive shaft extending therefrom;
   the one end of the drive shaft operable to releasably and slidably engage the intraosseous device such that the intraosseous device is rotatably fixed relative to the drive shaft;
   a motor disposed within the housing and rotatably engaged with the drive shaft;
   a power supply and electrical circuits operable to power the motor;
   a switch connected to the electrical circuits, the switch operable to activate the motor to rotate the drive shaft;
   a gear assembly rotatably attached to the motor;
   the drive shaft extending from the gear assembly opposite from the motor; and
   the gear assembly operable to reduce rotation of the motor,
   where the gear assembly is operable to reduce the rotation of the motor by a ratio between approximately sixty to one and eighty to one.

2. The powered driver of claim 1 further comprising an impact mechanism operable to allow the motor and an associated gearbox to function as an impact wrench whereby the impact mechanism may reduce the amount of power taken from batteries during insertion of an intraosseous device.

3. The powered driver of claim 1 further comprising a power circuit sensor operable to detect current changes indicating bone penetration by the intraosseous device.

4. The powered driver of claim 3 further comprising the power circuit sensor operable to automatically stop the driver once the intraosseous device has penetrated a cortex of the bone.

5. The powered driver of claim 1 further comprising a portion of the housing operable to be placed in a wall mounted charging system to provide a constant charge to the power supply.

6. The powered driver of claim 1 further comprising:
   a plurality of indicator lights including a red light operable to indicate low power levels in the power source;
   a yellow light operable to indicate satisfactory insertion torque and/or pressure; and
   a green light operable to indicate satisfactory power available in the power source.

7. The powered driver of claim 1 further comprising a red indicator light operable to indicate excessive torque and/or pressure on the drive shaft.

8. The powered driver of claim 1 further comprising a digital volt meter operable to indicate percentage of power available in the power source and number of insertions available without requiring recharging or replacement of the power source.

9. The powered driver of claim 1 further comprising a digital amp meter operable to indicate percentage of power available in the power source and number of insertions available without requiring recharging or replacement of the power source.

10. The powered driver of claim 1 where the switch and the electrical circuits are operable to rotate the drive shaft at a first low speed and a second higher speed.

11. The powered driver of claim 1 where the switch and the electrical circuits are operable to vary the speed of rotation of the drive shaft.

12. A powered driver operable to insert an intraosseous device into a bone and associated bone marrow comprising:
   a housing having one end of a rotatable drive shaft extending therefrom;
   the one end of the drive shaft operable to releasably and slidably engage the intraosseous device such that the intraosseous device is rotatably fixed relative to the drive shaft;
   a motor disposed within the housing and rotatably engaged with the drive shaft;
   a power supply and electrical circuits operable to power the motor;
   a switch connected to the electrical circuits, the switch operable to activate the motor to rotate the drive shaft; and
   a fiber optic cable extending from a light emitting diode to a halo light disposed on one end of the housing.

13. An apparatus operable to insert an intraosseous device into a bone and associated bone marrow and to assist with other medical procedures comprising:
   a powered driver having a housing with one end of a rotatable drive shaft extending therefrom;
   the one end of the drive shaft operable to releasably and slidably engage the intraosseous device such that the intraosseous device is rotatably fixed relative to the drive shaft;
   a motor disposed within the housing and rotatably engaged with the drive shaft;
   a power supply and electrical circuits operable to power the motor;
   a switch connected to the electrical circuits;
   the switch operable to activate the motor to rotate the drive shaft; and
   a suction pump having a connector operable to be releasably engaged with the one end of the drive shaft whereby the powered driver may operate the pump via rotation of the drive shaft.

14. A powered driver operable to insert an intraosseous device into a bone and associated bone marrow comprising:
   a housing having one end of a rotatable drive shaft extending therefrom;
   the one end of the drive shaft operable to releasably and slidably engage the intraosseous device such that the intraosseous device is rotatably fixed relative to the drive shaft;
   a motor disposed within the housing and rotatably engaged with the drive shaft;
   a power supply and electrical circuits operable to power the motor;
   a switch connected to the electrical circuits, the switch operable to activate the motor to rotate the drive shaft; and
   an impact mechanism operable to allow the motor and an associated gearbox to function as an impact wrench whereby the impact mechanism may reduce the amount of power taken from batteries during insertion of an intraosseous device.

15. The powered driver of claim 14 further comprising a power circuit sensor operable to detect current changes indicating bone penetration by the intraosseous device.

16. The powered driver of claim 15 further comprising the power circuit sensor operable to automatically stop the driver once the intraosseous device has penetrated a cortex of the bone.

17. The powered driver of claim 14 further comprising a portion of the housing operable to be placed in a wall mounted charging system to provide a constant charge to the power supply.

18. The powered driver of claim 14 further comprising:
   a plurality of indicator lights including a red light operable to indicate low power levels in the power source;
   a yellow light operable to indicate satisfactory insertion torque and/or pressure; and
   a green light operable to indicate satisfactory power available in the power source.

19. The powered driver of claim 14 further comprising a red indicator light operable to indicate excessive torque and/or pressure on the drive shaft.

20. The powered driver of claim 14 where the switch and the electrical circuits are operable to rotate the drive shaft at a first low speed and a second higher speed.

* * * * *